US 6,712,834 B2

(12) United States Patent
Yassour et al.

(10) Patent No.: US 6,712,834 B2
(45) Date of Patent: Mar. 30, 2004

(54) IMPLANTABLE BLOOD FILTERING DEVICE

(75) Inventors: Yuval Yassour, Haifa (IL); Ofer Yodfat, Reut (IL); Ygael Grad, Tel Aviv (IL); Moshe Rosenfeld, Beit Halevy (IL); Daniel Levin, Haifa (IL)

(73) Assignee: Mindguard Ltd., Caesarea (IL)

( * ) Notice: Subject to any disclaimer, the term of this patent is extended or adjusted under 35 U.S.C. 154(b) by 197 days.

(21) Appl. No.: 09/737,092

(22) Filed: Dec. 14, 2000

(65) Prior Publication Data
US 2001/0020175 A1 Sep. 6, 2001

Related U.S. Application Data

(63) Continuation of application No. PCT/IL99/00330, filed on Jun. 16, 1999.

(30) Foreign Application Priority Data
Jun. 16, 1998 (IL) ................................................ 124958

(51) Int. Cl.[7] .............................................. A61M 29/00
(52) U.S. Cl. ....................................................... 606/200
(58) Field of Search ............................... 606/200, 114, 606/127, 191, 192, 194, 198; 623/1.11, 1.12, 1.36

(56) References Cited

U.S. PATENT DOCUMENTS

| | | | | |
|---|---|---|---|---|
| 3,952,747 A | * | 4/1976 | Kimmell, Jr. ............... | 606/195 |
| 4,425,908 A | * | 1/1984 | Simon ......................... | 606/200 |
| 5,695,519 A | * | 12/1997 | Summers et al. ........... | 606/200 |
| 5,769,816 A | * | 6/1998 | Barbut et al. ............... | 606/200 |
| 5,911,734 A | * | 6/1999 | Tsugita et al. .............. | 606/200 |
| 6,152,946 A | * | 11/2000 | Broome et al. ............. | 606/200 |
| 6,171,328 B1 | * | 1/2001 | Addis .......................... | 606/200 |
| 6,179,859 B1 | * | 1/2001 | Bates et al. ................. | 606/200 |
| 6,241,738 B1 | * | 6/2001 | Dereume ................... | 623/1.11 |
| 6,336,934 B1 | * | 1/2002 | Gilson et al. ............... | 606/200 |
| 6,361,546 B1 | * | 3/2002 | Khosravi ..................... | 606/200 |
| 6,364,895 B1 | * | 4/2002 | Greenhalgh ................. | 606/200 |

* cited by examiner

Primary Examiner—Michael J. Milano
Assistant Examiner—Jessica R Baxter
(74) Attorney, Agent, or Firm—G.E. Ehrlich (1995) Ltd.

(57) ABSTRACT

An implantable filtering device for implanting within an artery supplying blood to the brain, the device being made of bio-compatible material and comprising a filtering unit for entrapping plaque debris, and an anchoring member engageable with the walls of the carotid artery for anchoring said filtering unit at a fixed location with the artery. The filtering unit has a tapering shape extending between a wide inlet portion and a narrower outlet portion extending downstream, and a tap element fitted at the outlet portion for entrapping plaque debris.

39 Claims, 18 Drawing Sheets

IMPLANTABLE BLOOD FILTERING DEVICE

This is a continuation of copending International Application PCT/IL99/00330 having an international filing date of Jun. 16, 1999.

FIELD OF THE INVENTION

This invention is in the field of implantable blood filtering devices, and more specifically it is directed to filtering devices for implantation in arteries supplying blood to the brain. The invention is also concerned with a method for detecting and removing plaque debris from the filtering device.

BACKGROUND OF THE INVENTION

Blood to the brain hemispheres is supplied by two carotid arteries, each of which branches-off into a so-called internal carotid and an external carotid. Blood to the brain stem is supplied by two vertebral arteries.

Cerebralvascular diseases are considered among the leading causes of mortality and morbidity in the modern age. Strokes denote an abrupt impairment of brain function caused by pathologic changes occurring in blood vessels. The main causes of strokes is insufficient blood flow to the brain (referred to as "an ischemic stroke") which are about 80% of stroke cases.

Ischemic strokes are caused by sudden occlusion of an artery supplying blood to the brain. Occlusion or partial occlusion (stenosis) are the result of diseases of the arterial wall. Arterial atherosclerosis is by far the most common arterial disorder, and when complicated by thrombosis or embolism it is the most frequent cause of cerebral ischemia and infarction, eventually causing the cerebral stroke.

Such disorders are treated in different ways such as by drug management, surgery (carotid endarterectomy) in case of occlusive disease, or carotid angioplasty and carotid stents as known in the art.

While endarterectomy, angioplasty and carotid stenting are procedures targeting at reopening the occluded artery, they do not prevent progression of new plaque (restenosis). Furthermore, embolisms from the new forming plaque in the internal carotid artery (with or without a stent implanted therein) can occlude smaller arteries in the brain and cause strokes. Even more so, the above treatment methods do not prevent proximal embolic sources, i.e. embolus formed at remote sites (heart and ascending aorta) to pass through the reopened stenosis in the carotid and occlude smaller arteries in the brain.

It will also be appreciated that endarterectomy is not suitable for intracarnial arteries or in the vertebrobasilar system since these arteries are positioned within unacceptable environment (brain tissue, bone issue) or are of a small diameter.

Introducing filtering means into blood vessels has been known for a while, in particular into veins. However, such filtering means are generally of a complex design which render such devices not suitable for implantation with carotid arteries and not suitable for handling fine plaque debris. However, when considering the possible cerebral effects of even fine plaque debris occluding an artery supplying blood to the brain, the consequences may be fatal or cause irreversible brain damage.

Occlusion of a vein is not a critical event and in most cases a time range of up to several hours is available before severe damage is caused to organisms. This applies also to arterial blood supply to the heart, which may survive a longer period of time before critical damage is caused.

However, in light of the short periods of time during which brain tissue can survive without blood supply (several minutes only, typically about 3 minutes), there is significant importance to provide filtering means suitable for entrapping even small plaque debris to prevent brain damage.

Whilst a large variety of patents in the field of inplantable filtering systems are known to Applicants, they are mostly intended for implantation in veins and in particular are intended for vena cava implantation. The following is a list of U.S. Pat. Nos., all being in the field of implantable blood filters: U.S. Pat. Nos. 5,391,196, 5,626,605, 5,827,324, 4,425,908, 3,996,938, 4,494,531, 4,619,246, 4,873,978, 4,817,600, 4,943,297, 4,957,501, 4,990,156, 5,059,205, 5,152,777, 5,324,304, 5,344,425, 5,370,657, 5,413,586, 5,549,626, 5,649,950, 5,695,519, 5,720,764, 5,800,525, 5,814,064, 5,800,525 and 5,709,704.

It is noted, however, that neither of the above patents refers to hemodynamic considerations which as appreciated by a skilled person are of critical importance. This is one of the reasons why, so far, filtering devices for implantation into carotid arteries are not available.

By using the term "hemodynamics" it is referred to blood flowing parameters which if not maintained may be fatal. Such parameters are, for example, wall shear stress, shear rates, pressure drop over the filter, platelet activation parameter (which is the dominant parameter governing blood coagulation). It is thus essential that such a filtering device does not change the hemodynamic parameters beyond some predetermined parameters.

It is the object of the present invention to provide an implantable filtering device for positioning in a blood vessel supplying blood to the brain so as to filter the blood and entrap embolic debris and thereby prevent extracranial embolus to occlude small intracranial arteries in the brain.

It is a second aspect of the present invention to provide a method for detecting plaque debris entrapped within the filtering device and a method for removal thereof.

SUMMARY OF THE INVENTION

According to the present invention there is provided an implantable filtering device for implanting within an artery supplying blood to the brain the device being made of bio-compatible material and comprising a filtering unit for entrapping plaque debris, and an anchoring member engageable with the walls of the carotid artery for anchoring said filtering unit at a fixed location within the artery;

the filtering device is characterized in that the filtering unit has a tapering shape extending between a wide inlet portion and a narrower outlet portion extending downstream, said outlet portion comprising a trap element for entrapping plaque debris.

The term "carotid artery" denotes any of the main arteries supplying blood to the brain. However, a preferred site for implanting such a filtering device would be the internal carotid artery, although not restricted thereto. Implanting a filtering device may also be possible within the carotid artery branches and in the vertebrobasilar system.

The device in accordance with the present invention is designed to retain some hemodynamic parameters and accordingly, the filtering unit is formed with a plurality of openings which are sized, shaped and disposed so as to ensure the following parameters:

i) 2<wall shear stress<$10^2$[dynes/cm$^2$]

ii) shear rate<5000 [sec$^{-1}$]

however, preferably, the shear rate is smaller than 2000 [sec$^{-1}$]. Furthermore, the pressure drop over the filtering device does not exceed about 20 mm Hg.

In a typical surgical procedure, the filtering device of the present invention is adapted for implanting within an internal carotid artery.

The trap element is adapted for trapping plaque debris which are filtered through the filtering unit. The trap element is a tubular body fixed to the filtering unit and comprises a plurality of deflectable trapping members radially extending within the body. The trapping members may also be arranged in a helical manner, extending inwardly from inner walls of the trap element. In accordance with one specific design, the trapping members constitute a maze and at a downstream end of the trapped member there are provided a plurality of deflectable end wires laterally extending across the end. In accordance with a most preferred embodiment, the trap element is cylindrical and coaxially extends at the outlet portion of the filtering unit. This particular design has significant importance in measuring flow parameters such as blood motion spectral signature and blood velocity profile. The trap element may also be formed with openings which may alternate in shape, depending on the desired flow pattern.

The arrangement is such that the end wires constitute a grid suitable for entrapping particles larger than about 100 $\mu$m. The trapping members and the end-wires of the trapped element are deflectable to removably accommodate a guide wire (catheter) therethrough for inserting and positioning the filtering device in sight.

By one particular application the trapping members are actually elastically deflectable to facilitate insertion of a vacuum catheter for suction of plaque debris entrapped within the trap element. This is a procedure which may be carried out periodically or upon detection of change of either or both the blood velocity profile and the blood motion spectral signature by means of non invasive detection means, such as ultrasound or micro CT equipment, as known per se.

In accordance with a preferred embodiment of the present invention, the filtering unit is made of a sheet of material formed with a plurality of openings. By one particular design, the openings of the filtering unit are horseshoe-like shaped oriented such that the legs thereof are upstream, which has performed improved hemodynamic performances. In accordance with still a preferred embodiment, at least part of the openings are formed with a flow directing element outwardly and inwardly projecting from the surface of the filtering unit. In the case of openings formed in the horseshoe-like shape, these flow directing elements are constructed by the middle portion thereof which are outwardly (or inwardly, respectively) directed.

The design of the filtering openings has influence on different blood flow parameters such as decrease of stagnation zones, prevention or decrease of pressure drop, prevention or decrease of flow detachment (thus prevention of swirls and vortices), control of filtration property, control of flow (velocity profile distribution) and its derivatives such as sheer stress, and controlling the flow profile over the filtering device and at its flow wake.

In accordance with one embodiment of the invention the anchoring member is integrally formed with the filtering unit. Alternatively, the filtering unit is removably connected to the anchoring member by leg members. In accordance with some preferred embodiments, the anchoring member is a stent as known per se which extends upstream with respect to said filtering unit.

In accordance with one preferred design, the engaging member is essentially cylindrical and is formed with at least two shell-like segments. In accordance with a particular design, one or more of the at least two segments are outwardly biased and are adapted for engagement with inner walls of the artery in which the device is implanted.

Typically, the filtering device is suitable for entrapping plaque debris larger than about 100 $\mu$m. The filtering unit may be designed in a variety of shapes, e.g. a wire braid essentially in the shape of a thimble, or a cone. Alternatively, the filter member may be a mashed screen made for example of Gortex™, or of an inert metal. The openings of the screen may have any practical shape e.g., triangular, rectangular, round, etc.

For practical reasons, the maximal diameter of a device which may be transferred through the arteries is about 3 mm. Accordingly, at least a portion of the filtering unit, and the anchoring member are inserted into the carotid artery at a collapsed state and are then deployed into an extended, operative position. Accordingly, at the collapsed state, the portion of the filtering unit and the anchoring member are received within a removable insertion tube. For that purpose, at the collapsed state the portion of the filtering unit and the anchoring member are wrapped in an overlapping manner about a longitudinal axis of the device. Alternatively, at the collapsed position, the portion of the filtering unit and the anchoring member are axially sectioned, with at least one of the sections being wrapped in an overlapping manner about the longitudinal axis.

It will be noted that portions of the filtering device which are less than about 3 mm in diameter do not have to be collapsed and accordingly, the filtering device may be constructed of two portions, a first, downstream portion which does not have to be collapsed and a second, upstream portion which includes a wider inlet portion of the filtering unit and the anchoring member which are collapsed prior to introducing into the arterial system.

According to one specific embodiment, one or both of the anchoring member and at least the portion of the filtering unit are self-expendable. This may be obtained by using suitable materials or designing the device at a special structure. Alternatively, one or both of the anchoring member and at least the portion of the filtering unit are balloon expandable.

Both these methods are known in the art of stent implantation. The filtering device of the invention may be introduced into the carotid artery either by percutaneous technique or at endarterectomy, also as known per se and as dictated by medical considerations.

In accordance with one specific embodiment, the filtering unit is retained within the stent as a replaceable member. In accordance with this embodiment, the filtering unit is essentially in the shape of a thimble, cone or dome and has at its edge two or more hook members for attachment within the stent. By another specific embodiment, the filtering unit is essentially in the shape of a thimble, a cone or a dome and has a tapering open end portion adapted for anchoring within a narrowing portion of the stent. However, both embodiments may be applied together. In accordance with such embodiments, the filtering unit is removable from the stent by collapsing the tapering portion thereof so as to disengage from the stent. Accordingly, the filtering unit may be withdrawn for replacement.

By another aspect of the present invention, there is provided a device for removing or replacing a filtering unit of the type which is removably anchored within the stent. Such a device comprises at least two flexible hooking members each formed with a sliding portion normally biased into radial expansion and terminating at a hook suitable for engaging the tapering portion of the filtering unit, the hooking members being displaceable between a retracted position and an expanded position; a manipulating collar slidingly engaged with the sliding portions; whereby axial displacement of the manipulating collar entails displacement of the hooking members, so as to engage, retract and then withdraw the filtering unit, and if required replace it by a new one.

Still another aspect of the invention is concerned with a method for detecting plaque debris entrapped within the trap element and removal thereof. In accordance with this method, the blood velocity profile and the blood motion spectral signature are detected by non invasive means such as ultrasound, micro CT, etc., and upon detecting the presence of plaque debris within the trap element, a suction catheter is inserted into the vicinity of the filtering device, into the trap element whereby the trapping members are temporarily outwardly displaced enabling suction of the plaque debris. However, upon removal of the suction catheter, the trapping members return to their original position (owing their elasticity) in which they extend inwardly within the trap element.

BRIEF DESCRIPTION OF THE DRAWINGS

In order to understand the invention and to see how it may be carried out in practice, some preferred embodiments will now be described, by way of example only, with reference to the accompanying drawings, in which:

in FIGS. 6B through 6H the anchoring member is illustrated in a simplified manner for sake of clarity;

FIG. 19 illustrate a flow velocity profile in association with a filtering device in accordance with the present invention, wherein:

DETAILED DESCRIPTION OF SOME PREFERRED EMBODIMENTS

Figure 1:
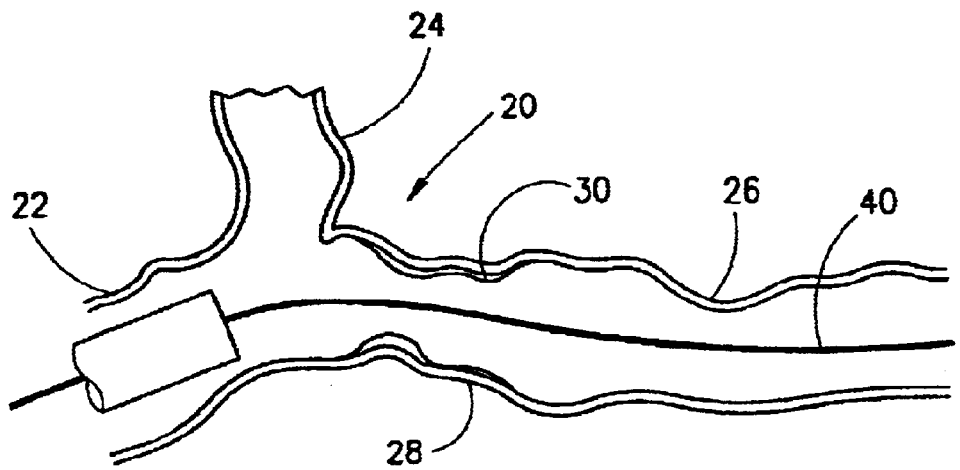
FIG. 1 is a schematic section through a portion of a partially occluded carotid artery through which a leading wire of a diagnostic catheter has been introduced.

In FIG. 1, a carotid artery generally designated 20 is shown in which the common carotid artery portion is designated 22, the external carotid designated 24 and the internal carotid designated 26. In the illustration of FIG. 1, right after branching-off, a partial occlusion (stenosis) of the internal carotid is illustrated at 28 in which calcification of plaque has accumulated at 30.

In such occurrences it is well known to insert a stent into the occluded portion 28 in a variety of percutaneous techniques which are safer the carotid endarterectomy, less traumatic, more cost-effective and useful also in particular for patients at high risk.

However, a problem with implanted stents is that after a while restenosis occurs where plaque accommodates on the stent and it is a serious danger that plaque debris (atheromatous plaque) may cause a stroke downstream the artery. In particular, such an event may occur during implantation of a stent. On the other hand, widening the artery by a stent, enables proximal thromboembolism (e.g. from the heart or the aorta) to flow through the stent and cause a stroke.

In order to prevent such occurrences, it is proposed to introduce a filter downstream the stent, which filter should preferably be deployed into an operative position prior to anchoring the stent.

Accordingly, a guide wire 40 is introduced by a percutaneous technique into the artery and then an introducing catheter 44 (see FIGS. 2A and 3C) is introduced into the artery guided by guide wire 40.

Figure 2A:
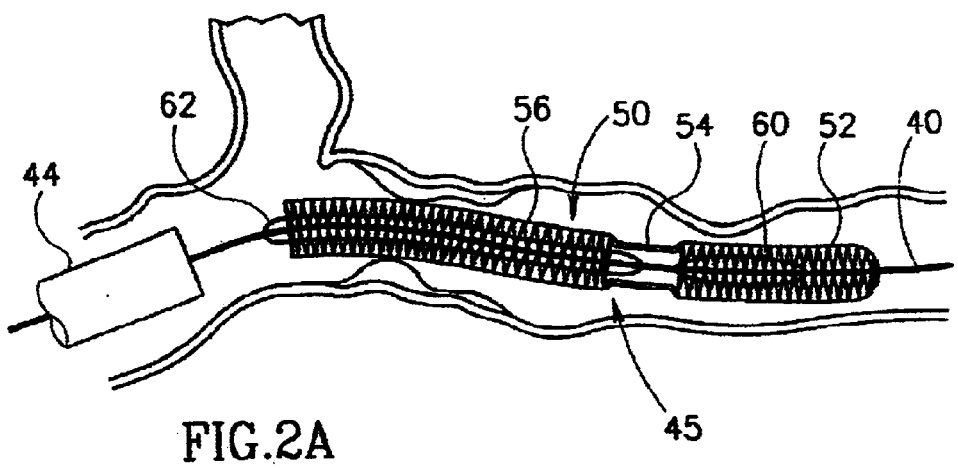
FIG. 2A is an embodiment of a device in accordance with the invention in a retracted position, superimposed with an balloon-type expanding device within the artery of FIG. 1.

An assembly comprising a filtering device generally designated 50 mounted in a retracted position over a balloon expanding unit 45 is introduced through the introducing catheter 44 into the position seen in FIG. 2A. The filtering device 50 comprises a filtering unit 52 which is generally in the shape of a thimble and is made of fine wire woven into a net having a mesh suitable for entrapping plaque debris of typically greater than about 100 μm, and connected by connecting legs 54 to an anchoring member 56 which in fact is a stent as known in the art. The device in accordance with the present embodiment is balloon expandable and as can be seen in FIG. 2A and better in FIG. 3C, the expanding unit 45 comprises a first balloon 60 and a second balloon 62, each being independently inflatable through suitable inflating tubes as will be explained in connection with FIG. 3C, and adapted for expanding the filtering unit 52 and the anchoring unit 56, respectively.

Figure 3A:
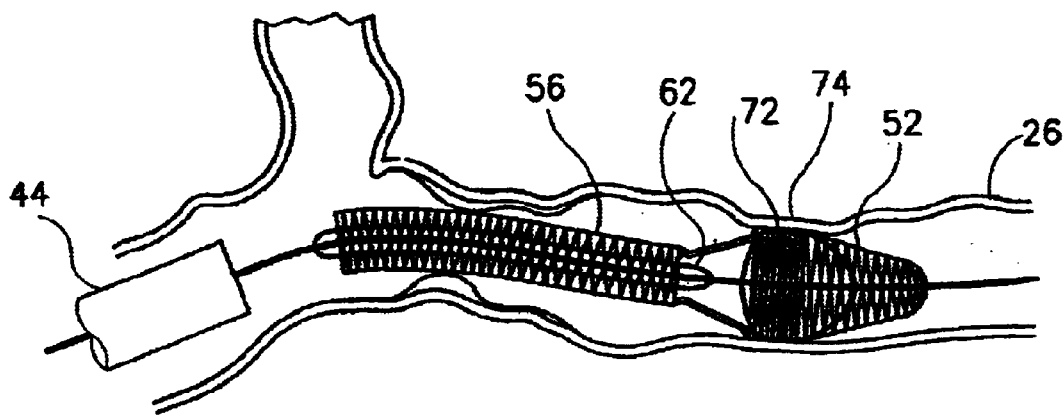
FIG. 3A illustrates a first stage of extending the filtering unit within the artery.
Figure 3B:
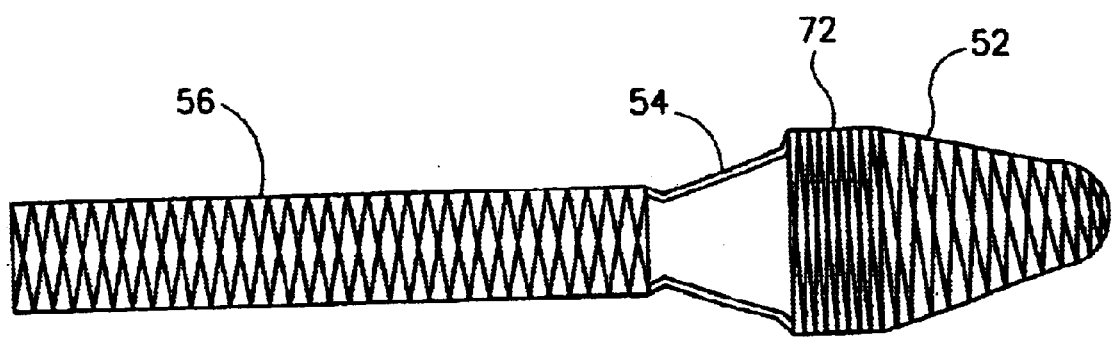
FIG. 3B illustrates the filter device of FIG. 2A after a first step of expanding the filtering unit.
Figure 3C:
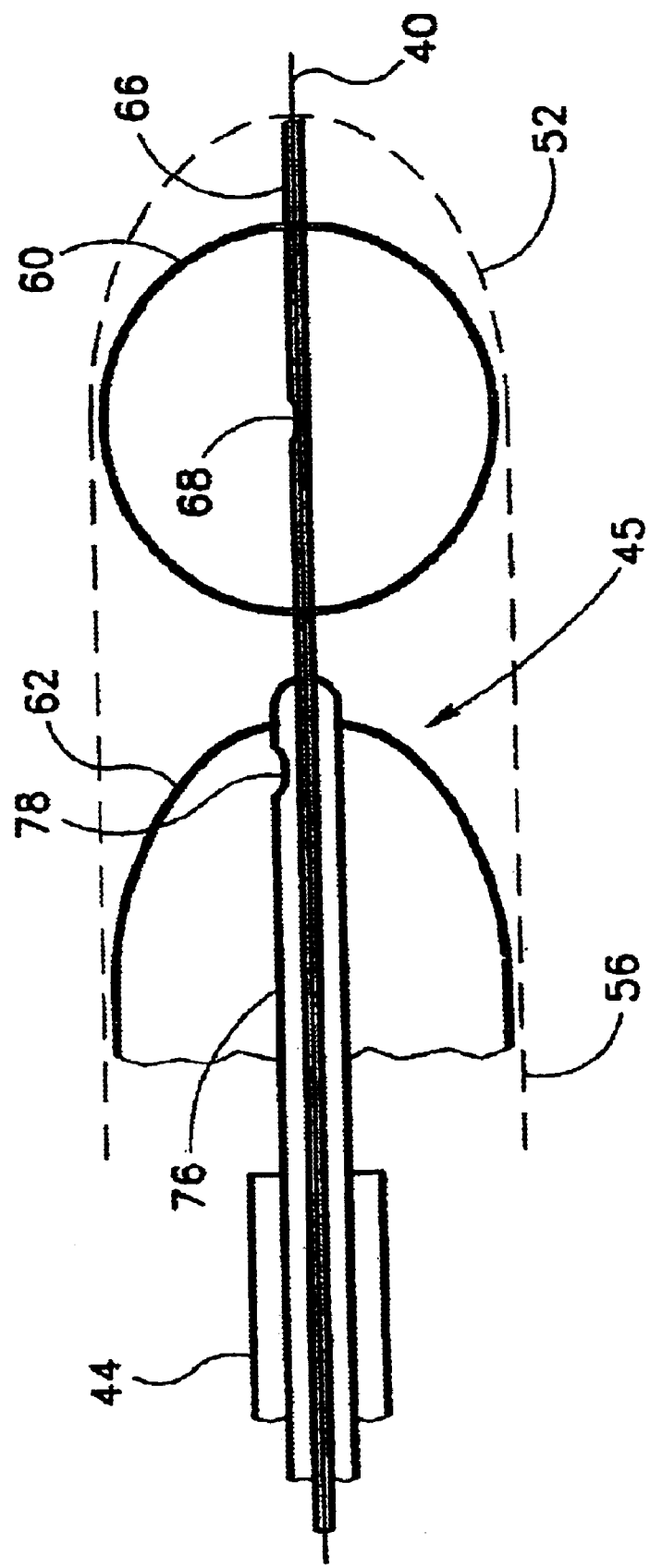
FIG. 3C is a section through a balloon-type expanding device for use in conjunction with a filtering device in accordance with the embodiment of FIG. 2B, the expanding device in its expanded position.

At a first stage of implanting the device, a fluid (air or suitable liquid) is pressurized through a first pressure tube 66 entailing expansion of balloon 60 via aperture 68, as a consequence of which the filter unit 52 expands into the position seen in FIGS. 3A and 3B, in which a rear portion 72 of filtering unit 52 engages with the inner walls of the internal carotid 26 at 74.

Figure 4A:
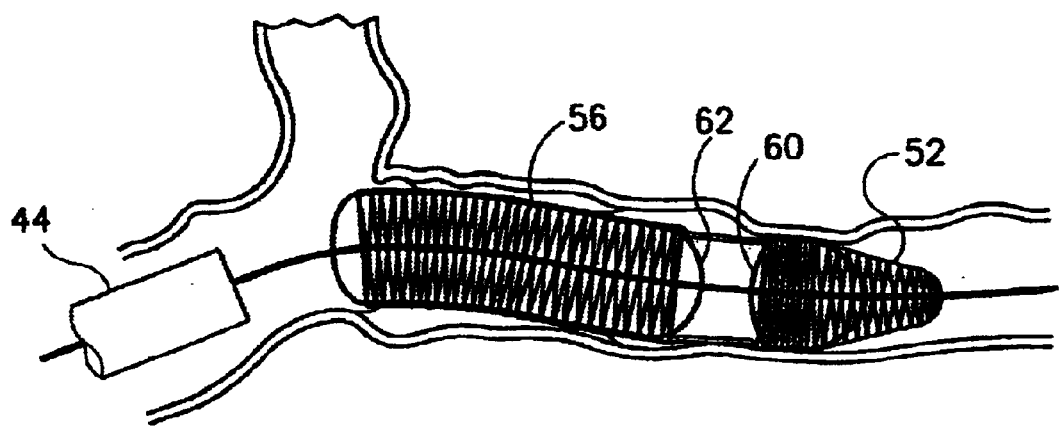
FIG. 4A illustrates the filtering device in a fully expanded position within the artery, prior to withdrawal of the balloon-type expanding device.

Once the filtering unit is positioned and expanded into its operative position as seen in FIG. 3A, then stent portion 56 is expanded into its operative position by inflating balloon 62 through a second inflating tube 76 formed with an opening 78, whereby the stent 56 is expanded into the position seen in FIG. 4A whereby it on the one hand dilates the calcified and occluded portion 28 of artery 26 and, on the other hand, serves as an anchor for filtering unit 52. Obviously, after concluding the expansion procedure, the expanding device is removed as known in the art.

Figure 4B:
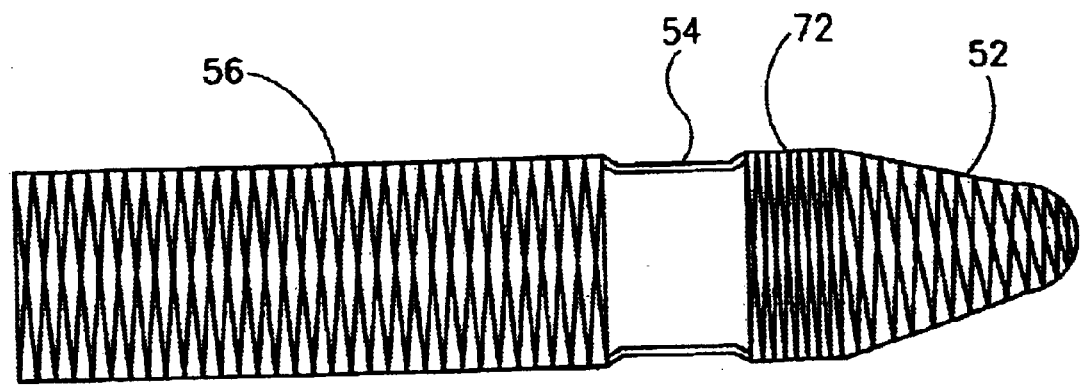
FIG. 4B is an illustration of the filtering device of FIG. 2B in a fully expanded position.

The filtering device of the invention is shown in FIG. 4B in its fully operative position in which both the filtering unit 52 and the anchoring member 56 are in their expanded position suitable for engagement within the inner walls of the artery.

Figure 5A:
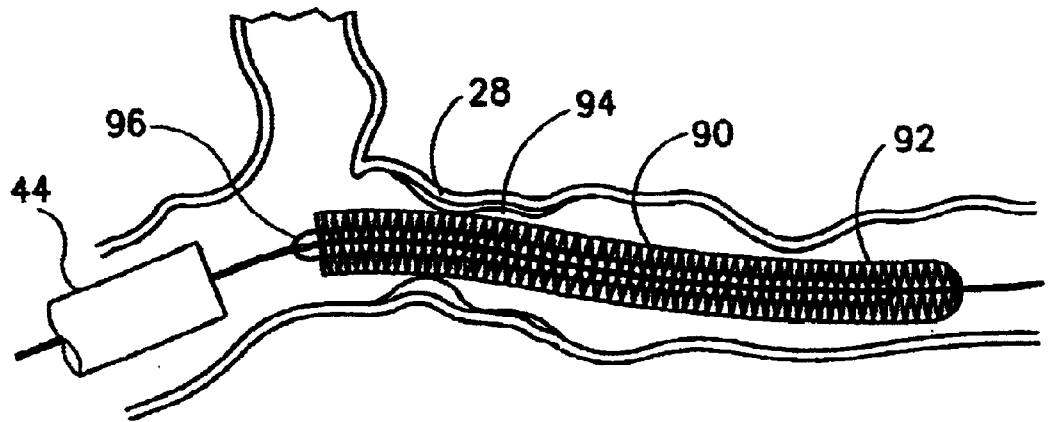
FIG. 5A illustrates a first step of insertion of a filtering device in accordance with another embodiment of the invention into a carotid artery.
Figure 5B:
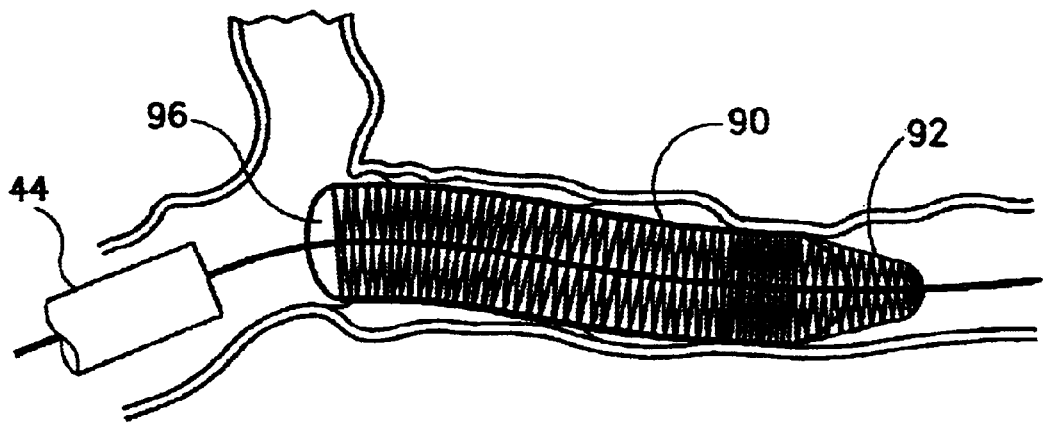
FIG. 5B illustrates the position of the filtering device seen in FIG. 5A after expansion.

Further attention is now directed to FIGS. 5A and 5B of the drawings illustrating a filtering device 90 in accordance with a modification of the invention. In accordance with this embodiment the filtering unit 92 is integral and continuously formed with the anchoring member 94 (which in fact serves as stent), rendering the device the shape of a sleeve having one closed end, namely at the filtering end. In accordance with this device, a single inflatable balloon 96 is used whereby at a single inflating operation of balloon 96 the filtering device is expanded into its operative position as seen in FIG. 5B. Thereafter, balloon 96 is deflated and altogether removed, with the filtering device 90 retained in its position after having applied radial, deleting force on the occluded artery portion 28 with simultaneous activation of the filtering portion 92 so as to entrap plaque debris which might disconnect from the occluded portion or from proximal sources.

Reference is now made to FIGS. 6A through 6H, illustrating a device in accordance with another embodiment of the present invention in which the filtering unit 100 is replaceable. At a first step, seen in FIG. 6A, an anchoring member 102 is positioned within the artery 104 by any of heretofore known techniques, e.g., percutaneous balloon expanding or self expanding metal, as known per Se. Anchoring member 102 is a sleeve-like stent with a front end 106 being slightly narrowed at portion 109 for the reason to become apparent hereinafter. At a second stage filtering unit 100 is introduced in a collapsed state through anchoring member 102 by an introducing manipulating catheter 107 fitted with an inflatable balloon 108, as explained hereinbefore in connection with previous embodiments.

Filtering unit 100 is a thimble-like metallic net, formed at its open end 112 with laterally projecting hooks 114. However, it will be appreciated that the net may be manufactured from a variety of other inertic material.

Figure 6A:
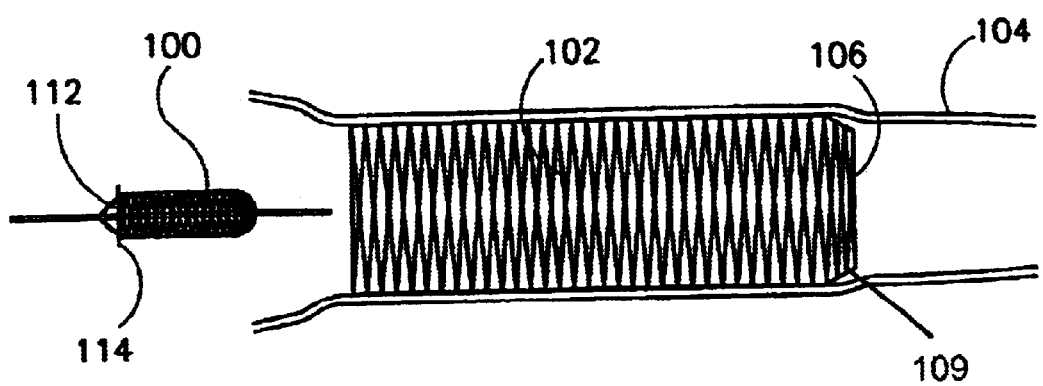
FIGS. 6A–6H illustrate consecutive steps of introducing a filtering unit into corresponding anchoring stent and replacement of the filtering unit.
Figure 6B:
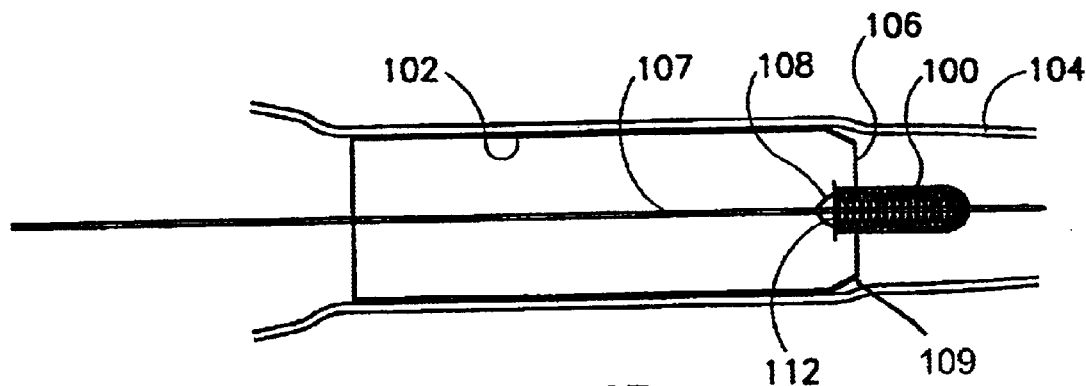
Figure 6C:
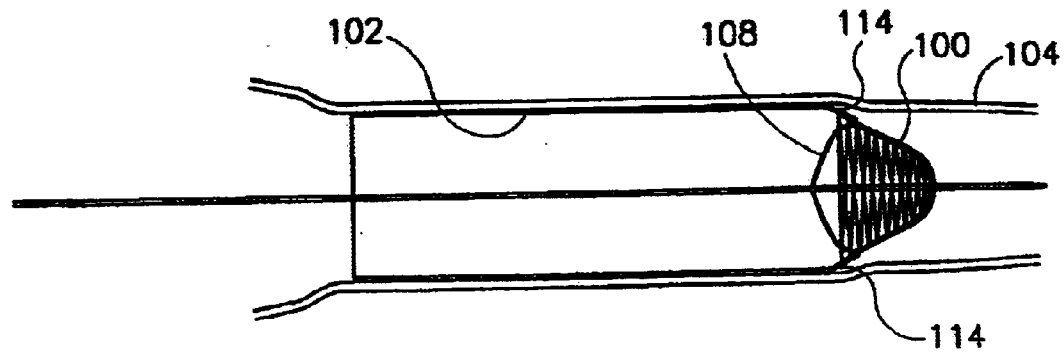

Typically all such procedures are carried out under suitable imaging inspection means and upon deployment of the filter unit 100 into a location adjacent the front end 106 of anchoring member 102, as seen in FIG. 6B filtering unit 100 is expanded into its operative position by inflation of balloon 108, as seen in FIG. 6C, whereby hooks 114 engage with the tapering portion 109 of the anchor member 102. Then, the balloon 108 is deflated and withdrawn, whereby the filtering device is in its operative position.

Figure 6D:
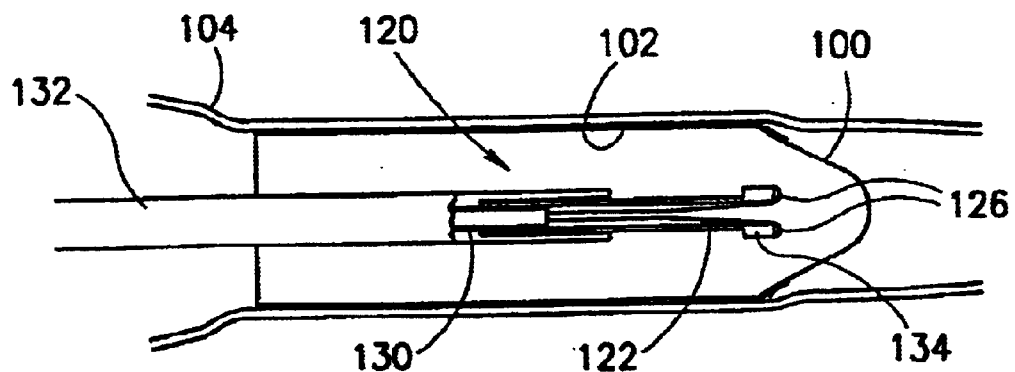

Either periodically or upon detecting accumulation of plaque on the filter 100, a procedure may be carried out for replacement of the filtering unit. For that purpose a suitable device 120 is percutaneously introduced through artery 104 and to a position as seen in FIG. 6D. Device 120 comprises two flexible hooking members 122 (best seen in FIG. 6E) each formed with a sliding portion 124 which is normally biased radialy outwardly and comprises a hook-like end 126. Both hooking members 122 are connected at their other end to a manipulating wire 130 which is axially displaceable within a catheter 132. A manipulating collar 134 is axially displaceable within catheter 132 and embraces the hooking members 122. The arrangement is such that axial displacement of manipulating collar 134 entails displacement of the hooking members 122 between a retracted position in which the hooking members are essentially straight and the hooks 126 are received by collar 134 (see FIG. 6D), and an expanded position in which the hooking members 122 are radially expanded and the hooks 126 are exposed (see FIG. 6E).

Figure 6E:
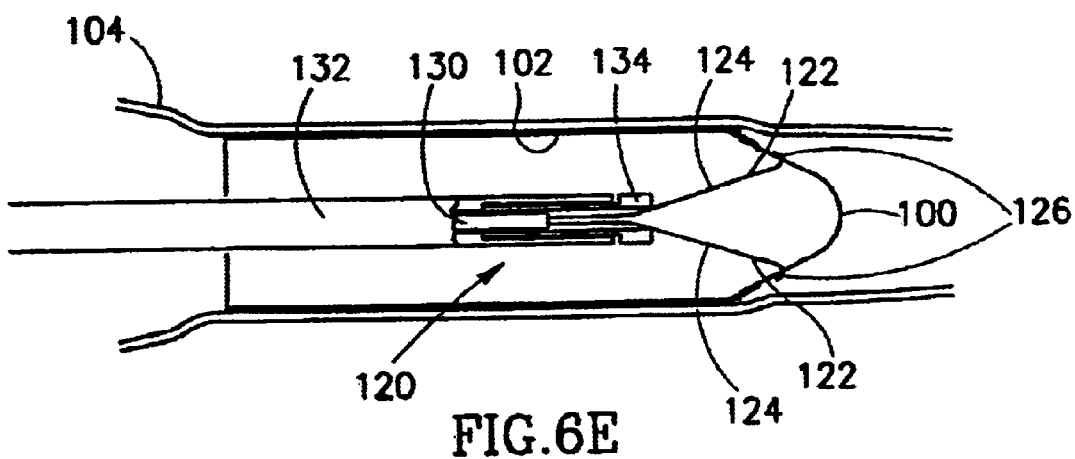
Figure 6F:
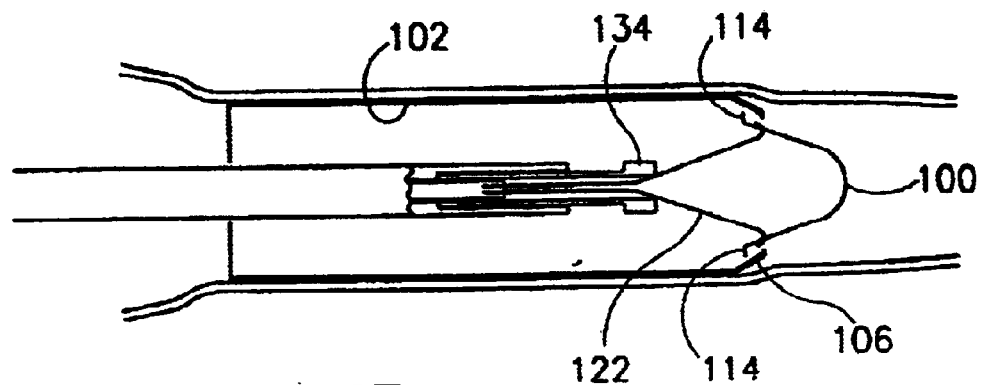

Upon insertion of device 120 into the anchoring member 102 and positioning it as seen in FIG. 6D, the hooking members are displaced into their expanded position as seen in FIG. 6E, whereby the hooks 126 engage with the filtering unit 100. However, withdrawal of the filtering unit 100 is possible only after retraction. Accordingly, manipulating collar 134 is axially extracted, as seen in FIG. 6F, entailing gradual displacement of the hooking members 122 into their retracted position, whereby filtering unit 100 collapses with hooks 114 disengaging from the narrowed portion 106 of the anchoring member 102.

Figure 6G:
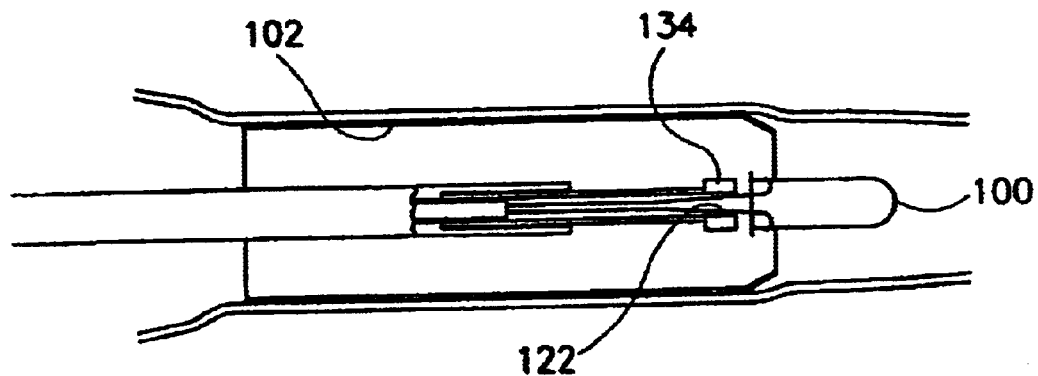
Figure 6H:
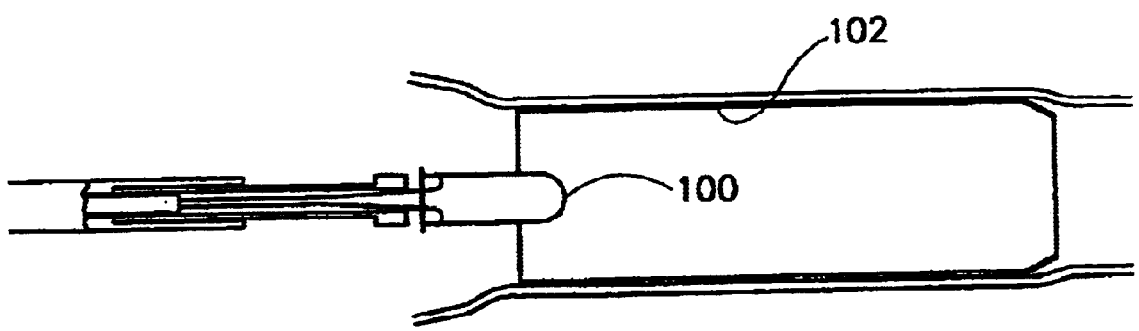

Upon completing the axial extraction of the manipulating collar 134, as seen in FIG. 6G, the hooking members 122 are completely retracted with the is filtering unit 100 entirely collapsed and disengaged from the anchoring member 102. In this position, the filtering unit 100 may be removed from the anchoring member 102 and withdrawn altogether.

Replacement of a fresh filtering unit is carried out in a reversed sequence of operation as explained hereinabove can be readily appreciated by a skilled person.

Figure 7A:
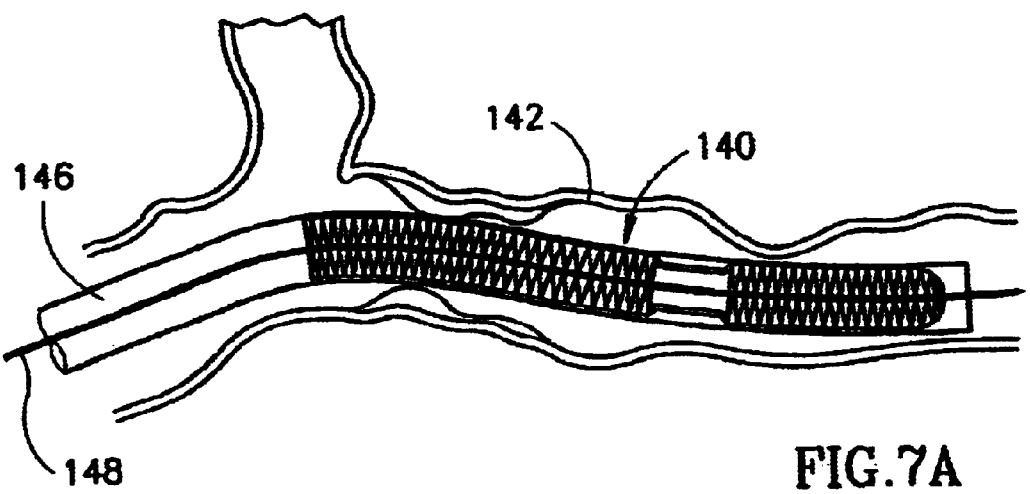
FIGS. 7A–7C illustrates consecutive steps of deploying a self expandable filtering device in accordance with another embodiment of the invention.
Figure 7B:
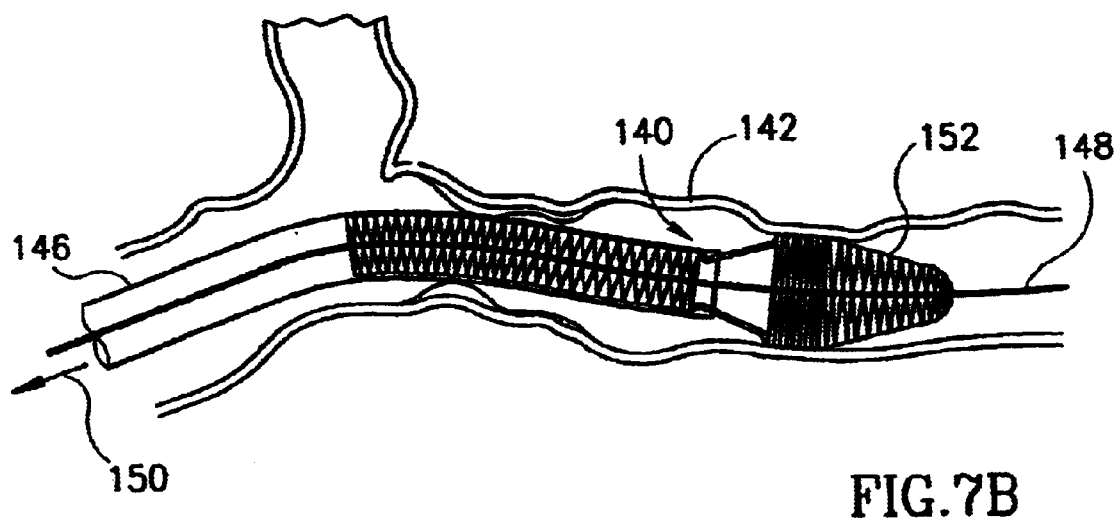
Figure 7C:
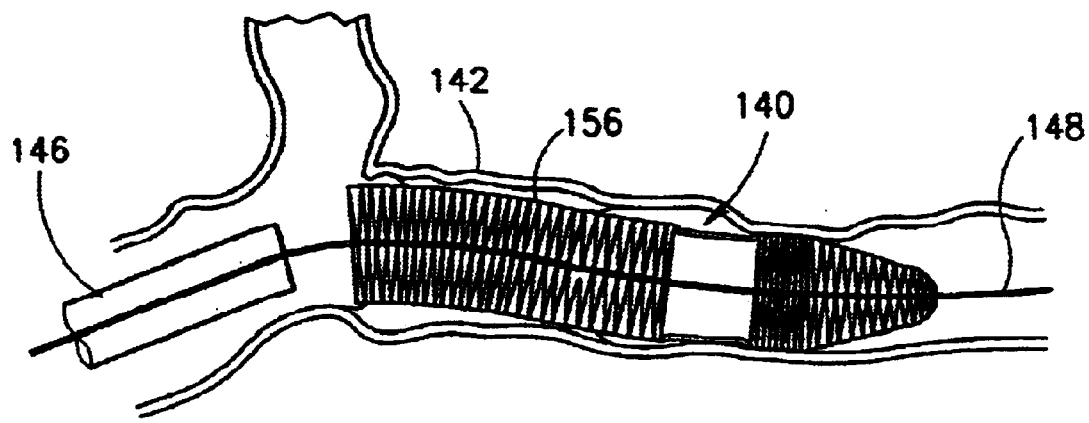

FIGS. 7A–7C illustrate the consecutive steps of deploying a self-expandable filtering device 140 into an internal carotid artery 142.

Figure 2B:
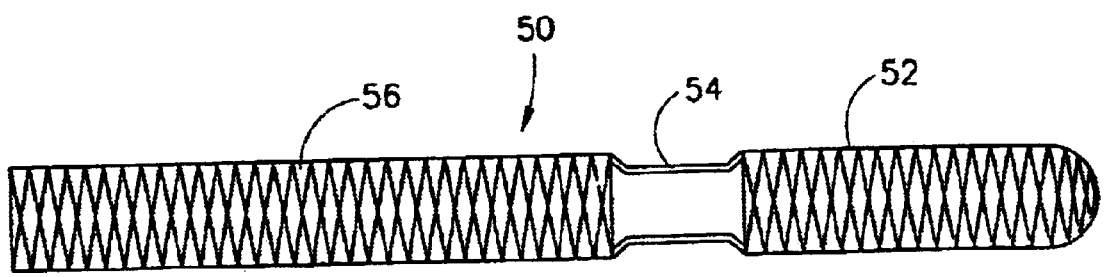
FIG. 2B is a view of a device in accordance with one embodiment of the present invention, the device shown in a retracted position.

The self-expanding filtering device 140 is typically made of a metallic web which in its collapsed state resembles the filtering unit 50 seen in FIG. 2B. However, filtering device 140 is biased to spontaneously expand into its operative position seen in FIG. 7C. At an initial position seen in FIG. 7A, the filtering device 140 is collapsably retained within a deploying sleeve 146 which is introduced into the artery 142 over a guide wire 148, as known per se.

At a second stage, seen in FIG. 7B, the deploying sleeve 146 is withdrawn in the direction of arrow 150 whereby the filtering unit 152 spontaneously expands to its operative position in which a portion of the filtering unit engages the walls of the artery 142. Further withdrawal of the deploying sleeve 146 exposes the entire filtering device 140, wherein the anchoring member 156 expands into an anchoring position within the artery 142 wherein the filtering device 140 is ready for use. The, the deploying sleeve 146 and guide wire 148 are removed as can readily be understood.

Figure 8:
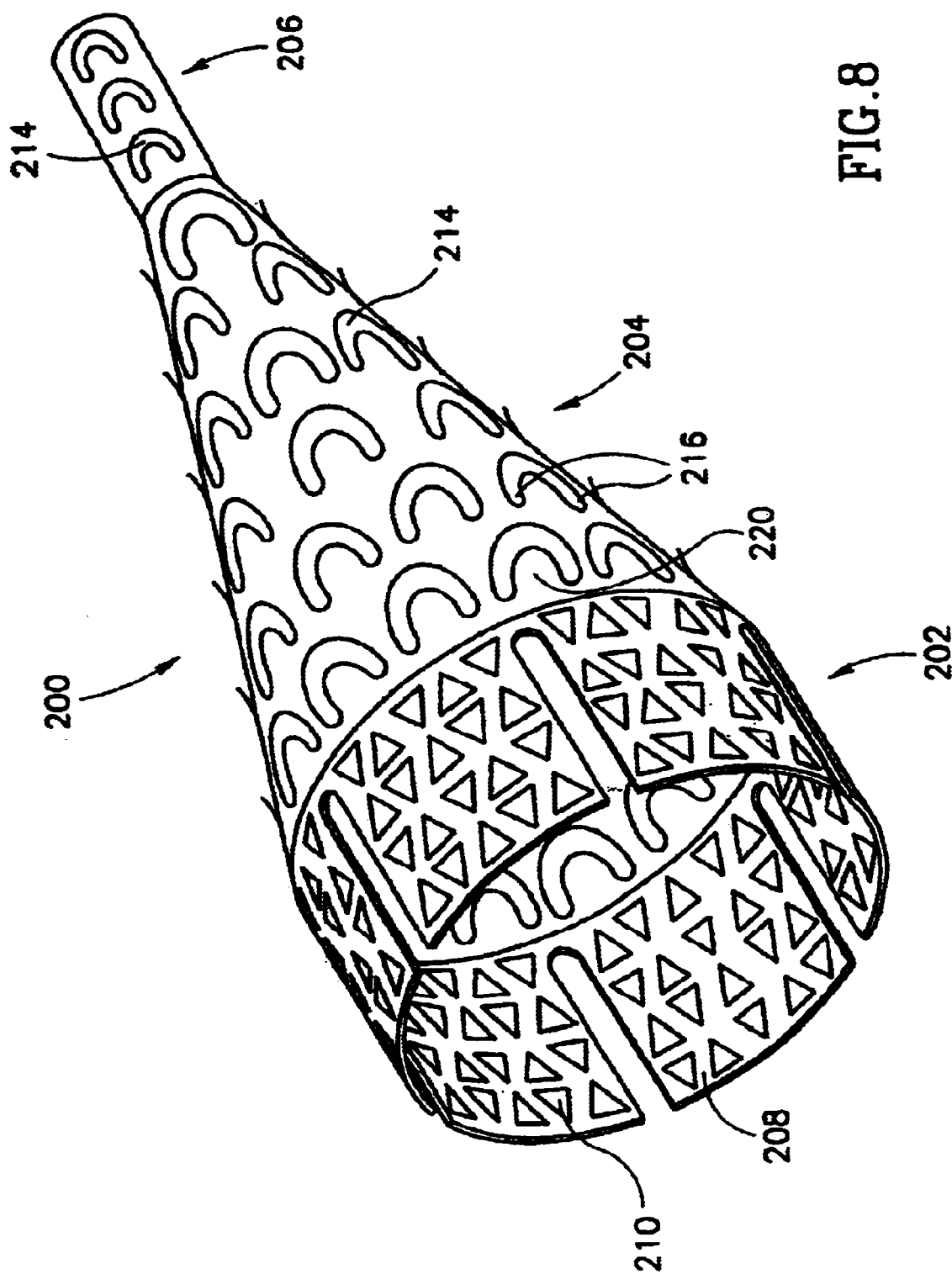
FIG. 8 is an isometric view of a filtering device in accordance with a preferred embodiment of the present invention.

The embodiment of FIG. 8 illustrates a filtering device generally designated 200 which is a preferred embodiment of the present invention. The filtering device 200 is formed of an anchoring member 202, a filtering unit 204 having a tapering cross-section between a wide inlet articulated to the anchoring member 202 and a narrow outlet to which is connected a cylindrical, coaxial trap element 206.

The device is made of a biocompatible material as discussed above and in the present example the three portions, namely anchoring member 202, filtering unit 204 and trap element 206 are integrally formed with one another or fixedly attached to one another. The anchoring member 202 is made of six segments 208 and as can better be seen in FIG. 9, these segments are slightly outwardly biased for engagement within the artery and fixation of the filtering device at the desired location. It is noted that the anchoring member 202 is formed with a plurality of triangular openings 210 which do not play any particular role in the filtering process but rather are meant for improving grip within the inner walls of the artery. Accordingly, these openings may have different shapes and different distribution.

Figure 12:
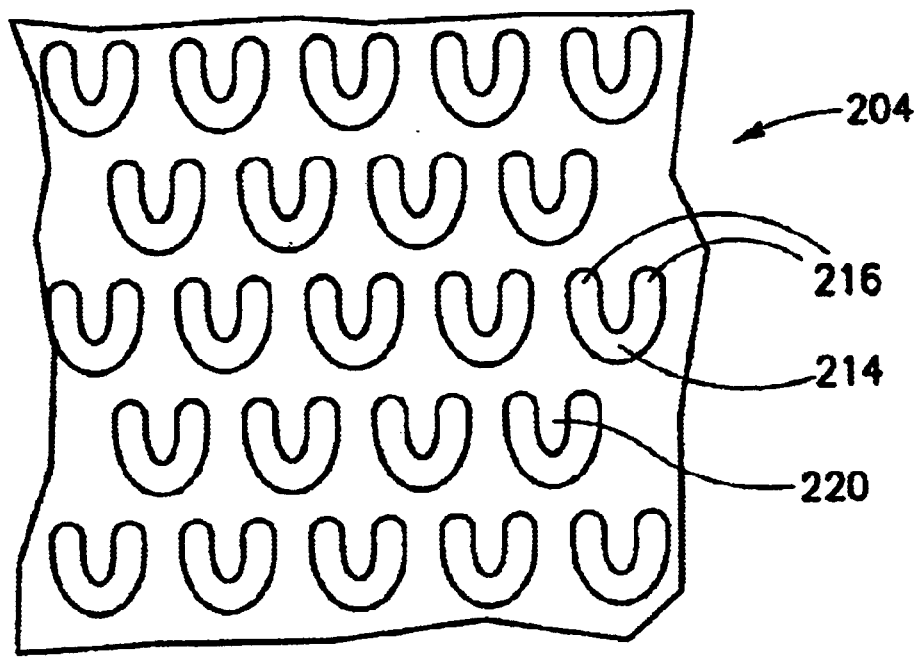
FIG. 12 is a portion of the filtering unit of the filtering device seen in FIG. 8.

Referring now to the filtering unit 204, it is provided with a plurality of horseshoe-like shaped openings 214 with their leg portions 216 extending upstream. The distribution, the size, the shape and orientation of these openings is determined in accordance with hemodynamic parameters which are desirely retained, as explained hereinbefore and the reader is directed to FIGS. 12 and 13 illustrating some preferred parameters of these openings.

Each of the horseshoe-like openings has a middle leg portion 220 slightly outwardly (or inwardly, as may be the case) projecting from the surface of the filtering unit 204, serving as a directing element for improving the flow parameters at the vicinity of the filtering device. The flow directing element 220 can best be seen in FIG. 13B. It will be understood that the flow directing elements at different zones of the filtering unit may be deflected either inwardly or outwardly, depending on a variety of hemodynamic considerations.

Figure 9:
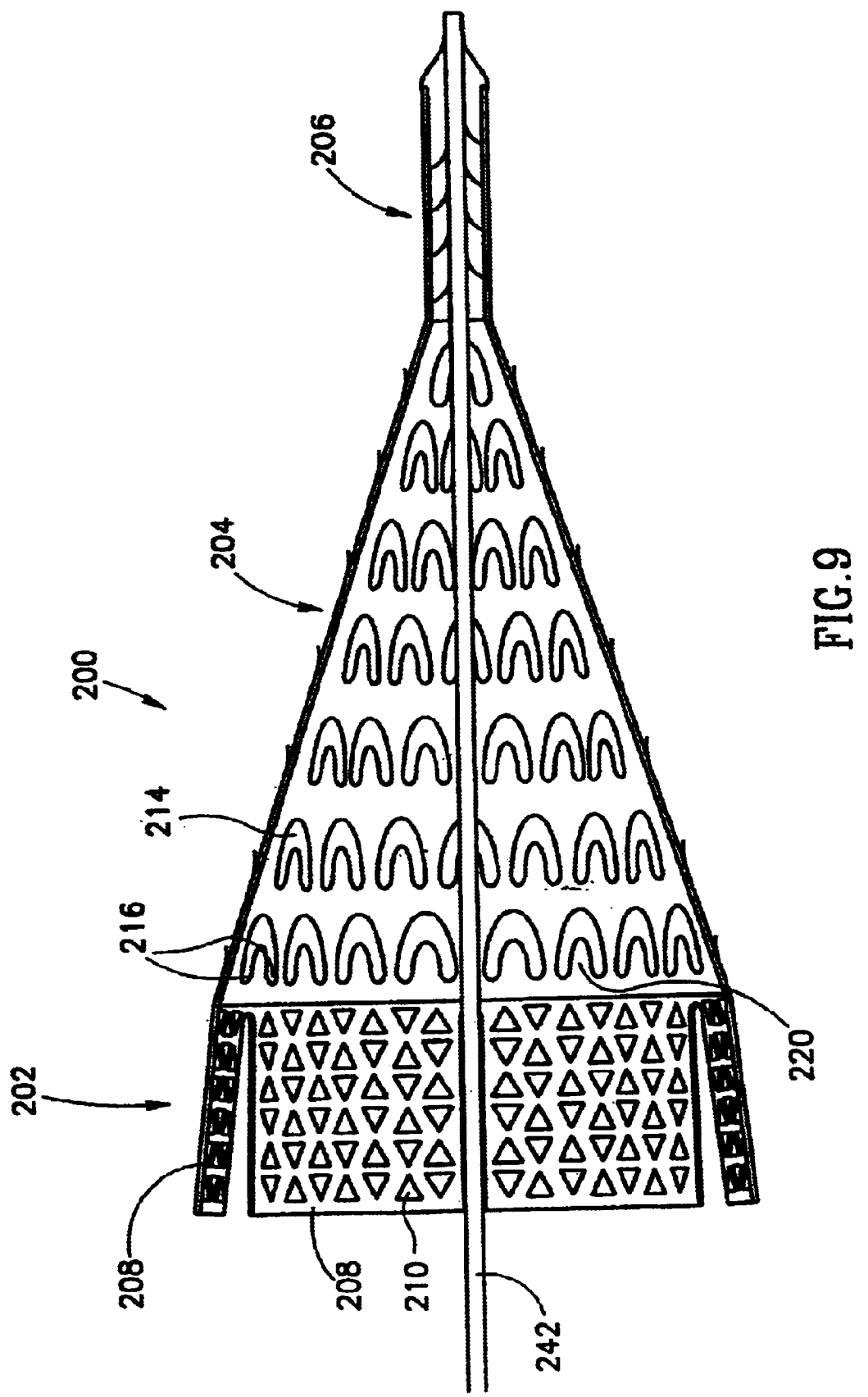
FIG. 9 is a sectional view through a filtering device as in FIG. 8, with a portion of a guide wire extending therethrough.

As can further be noticed in FIGS. 8 and 9, the trap element 206 is also formed with openings 214 similar to those formed at the filtering unit 204. However, these openings may be omitted or alternate in shape, depending on the desired flow pattern.

The trap element is designed for trapping plaque debris which enter the filtering unit, and which owing to the essentially unidirectional blood flow, are drifted into the trap element where thy are entrapped by the trapping members, preventing the plaque debris from flowing upstream to the filtering unit. The trap element is provided for trapping plaque derbies which are screened at the filtering unit but after a while might have passed through the openings of the filtering unit.

Figure 10:
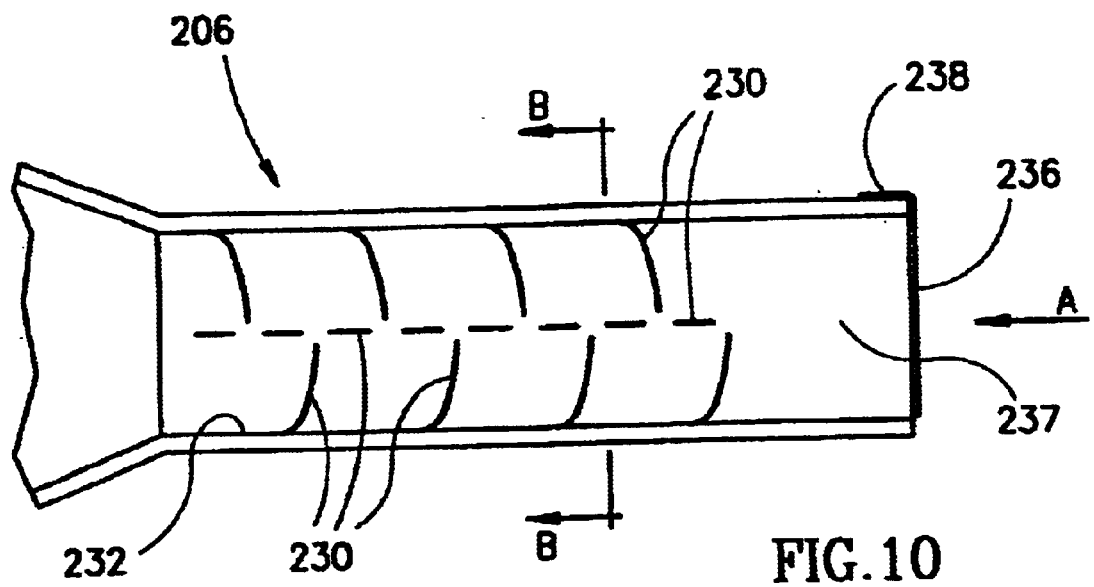
FIG. 10 is a schematical sectional view through a trap element of a filtering device of the invention.
Figure 11A:
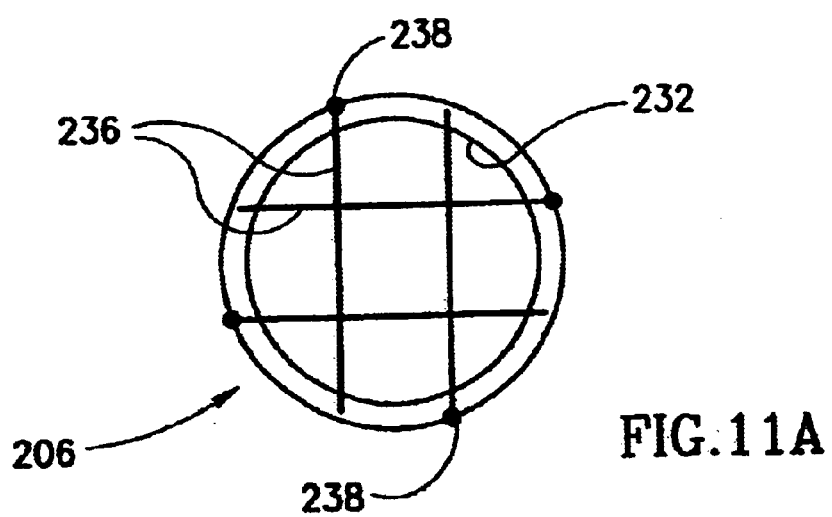
FIG. 11A is an elevation from the direction of arrow A seen in FIG. 10 (for the sake of clarity, the trapping members are not shown)
Figure 11B:
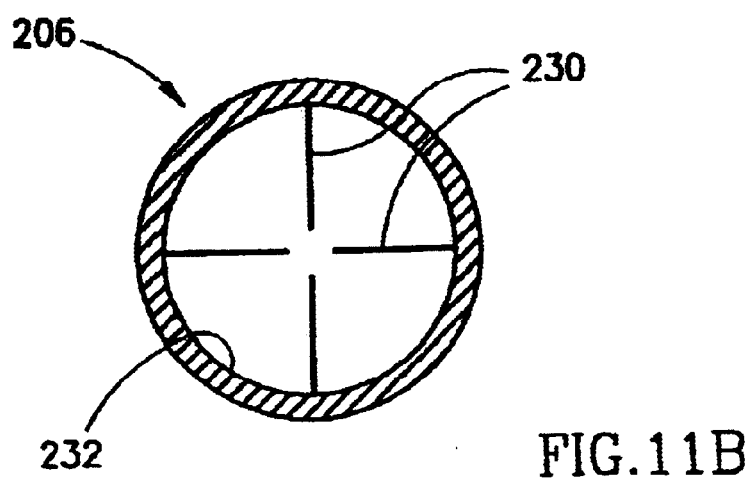
FIG. 11B is a schematical sectional view through line B—B in FIG. 10.

Further reference is now made to FIGS. 10 and 11 for better understanding the design of the trap element 206. As can be seen, the cylindrical body of the trap element 206 is formed with a plurality of trapping members 230 radially extending from the inner wall 232 of the trap element 206. As seen in FIG. 10, the filtering members 230 are arranged in a staggering manner (i.e. do not extend one opposite another) and as seen in FIG. 11B, they extend almost to a center-line of the trap element 206.

Obviously, the trapping members seen in FIG. 11B may differ in shape, size and distribution within the trap element. Alternatively, the trapping members may be disposed along a helical path, inwardly extending from the inner wall of the trap element. By one particular application, the trapping members are laser-cut from the wall of the trap element and are than bend inwardly, after plastically annealing. As will become apparent with reference to FIG. 20, this method of manufacture involves also a functional advantage, namely, perforating the wall of the trap element for accommodating the trapping members in their deformed position.

Mounted at the end of the trap element 206 there are fixed several end wires 236 each having one end thereof fixed to the trap element at 238 (see also FIG. 11A) the opposite end of each of these end wires being free. The arrangement is such that the end wires 236 are normally at rest over the end of the trap element and form a grid suitable for entrapping particles larger than about 100 μm.

It is noted, in particular in FIG. 10, that there is a space 237 between the end wires and trapping members, for accommodating entrapped plaque debris.

The trapping members 230 and the end wires 236 are elastic members biased to retain the position as illustrated and explained above. However, their elasticity provides for introducing a guide wire (at times referred to as guide catheter) seen in FIG. 9 and designated 242. This guide wire saves for introducing and positioning the filtering device, as explained herein before. However, flexibility of the trapping members is of importance also for removal of plaque debris entrapped within the trap element as will be explained hereinafter.

Figures 13A, 13B:
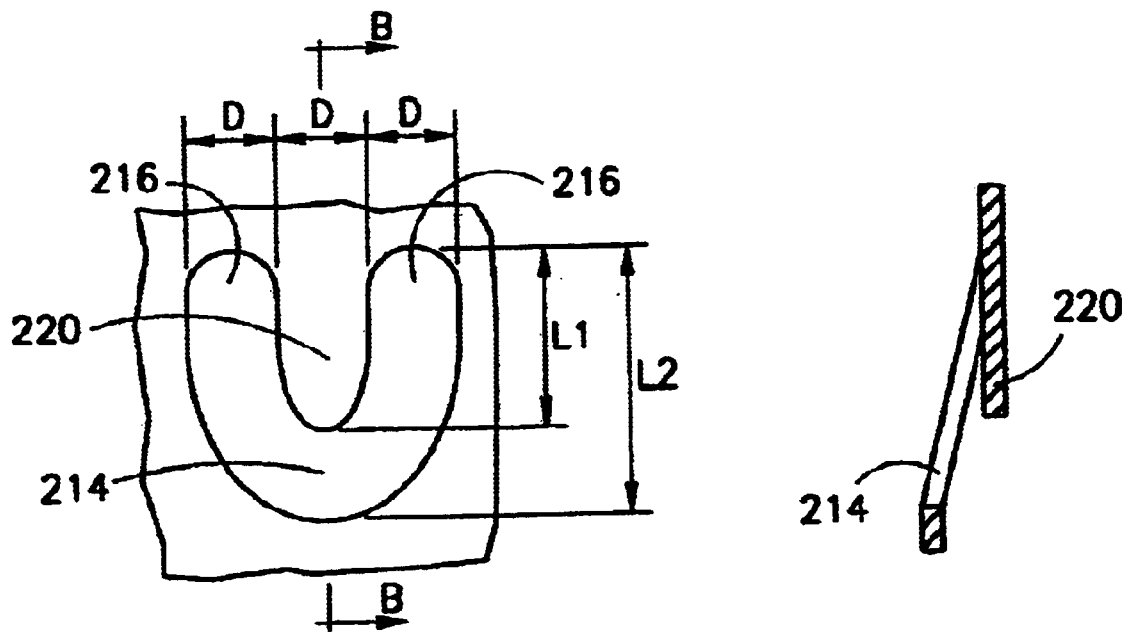
FIG. 13A is a detailed view of an opening formed in the filtering unit seen in FIG. 12.
FIG. 13B is a side view of the portion seen in FIG. 13A.

FIG. 12 is a planar view of a portion of the filtering unit 204 in which the openings in accordance with a preferred embodiment are seen. For filtering particles of about 100 μm, it was found that the opening, seen in larger scaling in FIG. 13A shows best performances when L1=about 0.22 mm; L2=0.3 mm; D=about 0.1 mm.

It was also found that a conical filtering unit having a tapering rate of about 1:6 of the 204 is hemodynamically optimal. However, a tappering rate within the range of 1:4–1:8 is also suitable. As mentioned above, the central leg portion 220 extending between legs 216 of each opening are preferably outwardly (or inwardly, as may be the case) directed for generating some flow vectors in a desired direction.

It should be appreciated that the ratio between the above parameters, is kept for handling plaque debris particles of other size.

Figure 14A:
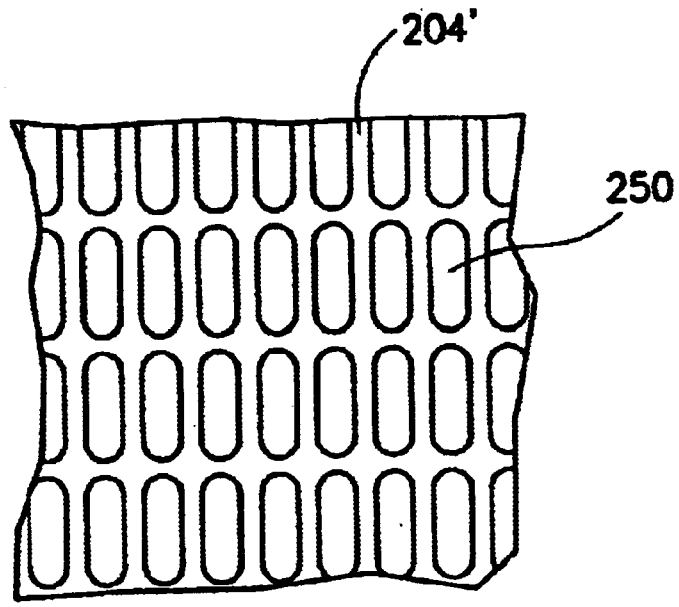
FIGS. 14A and 14B are portions of openings of a filtering unit in accordance with another embodiment of the invention.
Figure 14B:
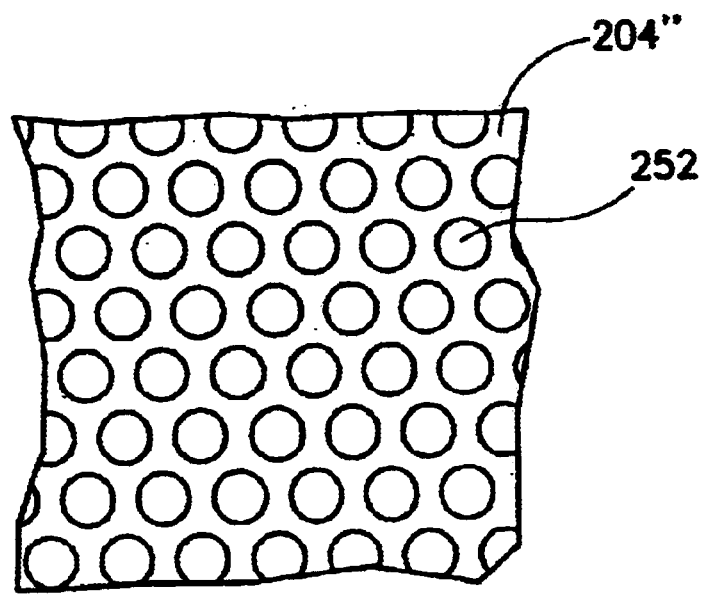
Figure 15A:
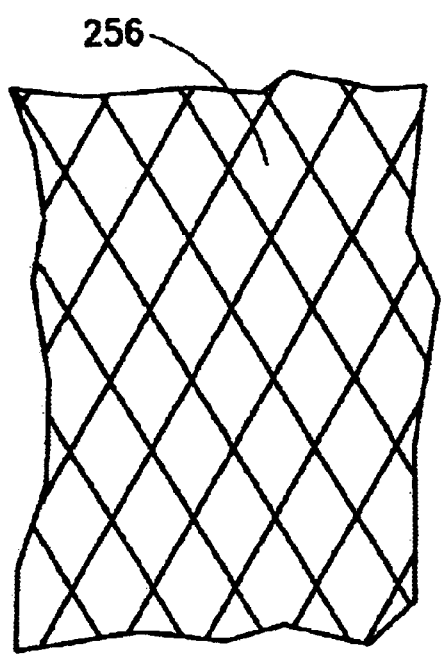
FIGS. 15A–15D are different examples of openings in a filtering unit constructed by a grid of wires in accordance with another embodiment of the invention.
Figure 15B:
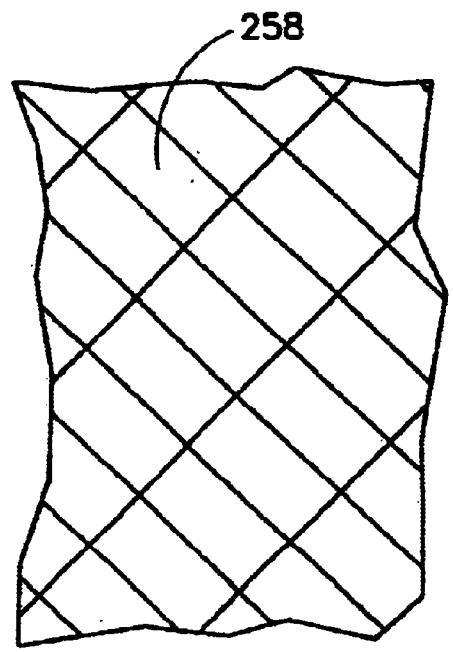
Figure 15C:
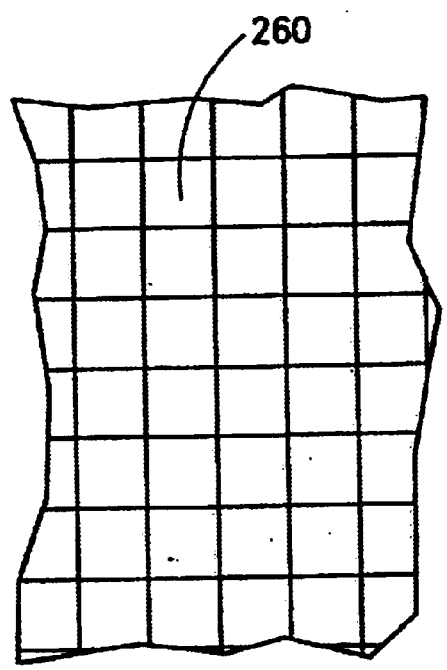
Figure 15D:
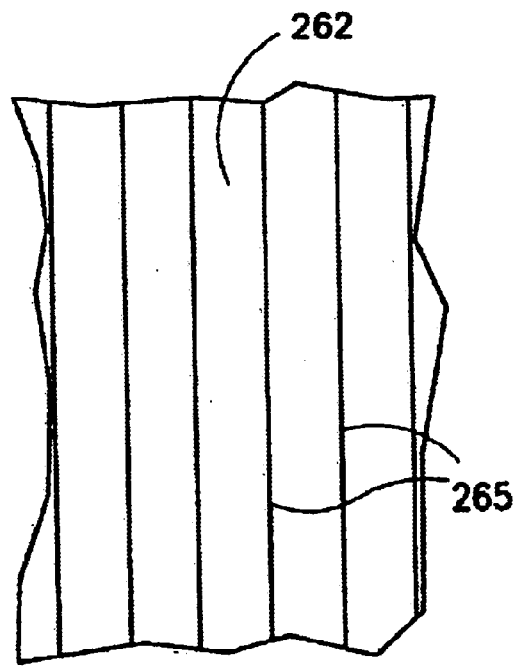

FIG. 14A is a portion of a filtering unit 204' wherein the openings 250 have an elongated shape with rounded ends. In FIG. 14B, the portion 204" is formed with essentially circular openings 252. One will appreciate that the openings may be formed at a variety of other shapes as well, depending on the desired flow and filtering parameters which are required of the device.

Further attention is now directed to FIG. 15 of the drawings in which a different manner of constructing the filtering unit is shown. In accordance with this embodiment, the mesh of the filtering unit is constructed by a grid of wires forming openings in a variety of shapes. It will be appreciated that in accordance with such embodiments, there may be provided some support means, e.g. bends or reinforcing straps extending along the filtering unit. In FIG. 15A, the openings 256 have a robust-like shape, in FIG. 15B, the openings 258 are rectangular, in FIG. 15C, the openings 260 are essentially square and in FIG. 15D, the openings 262 are in fact formed between a plurality of adjacent wires 265 tensioned about the enveloping contour of the filtering unit.

Figure 16:
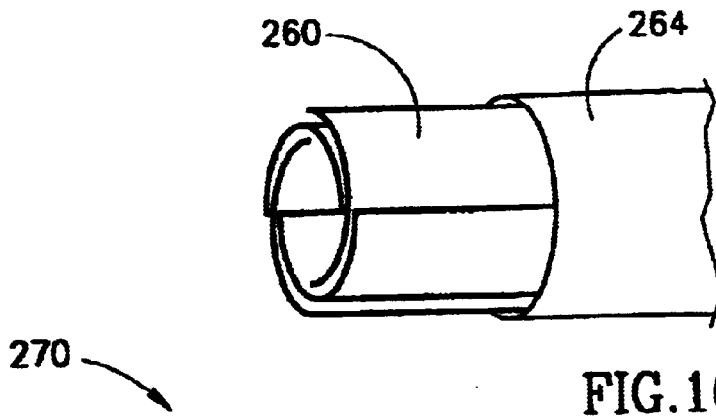
FIG. 16 illustrates a first method of collapsing the device of the invention, seen within a collapsing sleeve.

The actual diameter of a device which may be passed through the arteries of an individual should not exceed about 3 mm. For that purpose, it is desired that wider portions of the device, namely the rear portion of the filtering unit 204 and of the anchoring member 202, be reduced to a practical diameter. This may be achieved in several ways. In a first manner, as illustrated in FIG. 16, the filtering unit 204 and the anchoring member 202 are divided into axially extending sections 260 which are allowed to be collapsed in an overlapping manner, whereby the device may be introduced into a cylindrical sleeve 264, retaining the filtering device in its collapsed state until it is deployed into its operative position by retraction of sleeve 264 by means of the guide wire.

Figure 17:
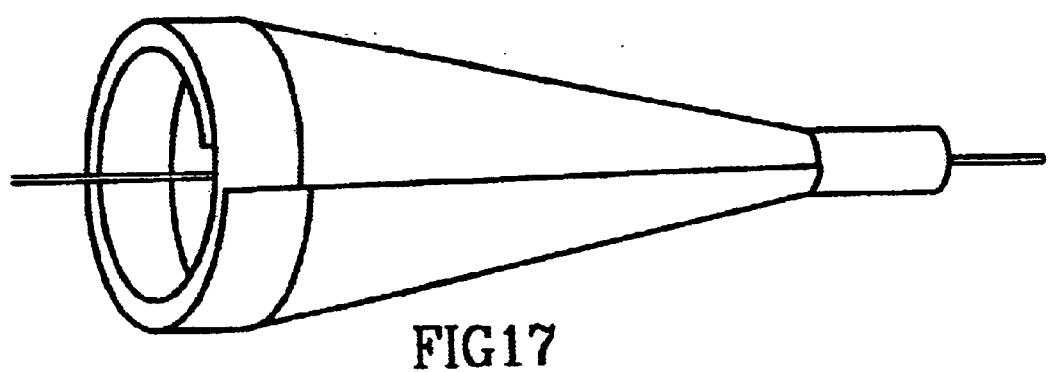
FIG. 17 is a second method for collapsing the device of the invention.

In the embodiment of FIG. 17, the filtering device 270 is wound in an overlapping manner about its longitudinal axis so as to retain a maximal diameter not exceeding about 3 mm.

Figure 18A:
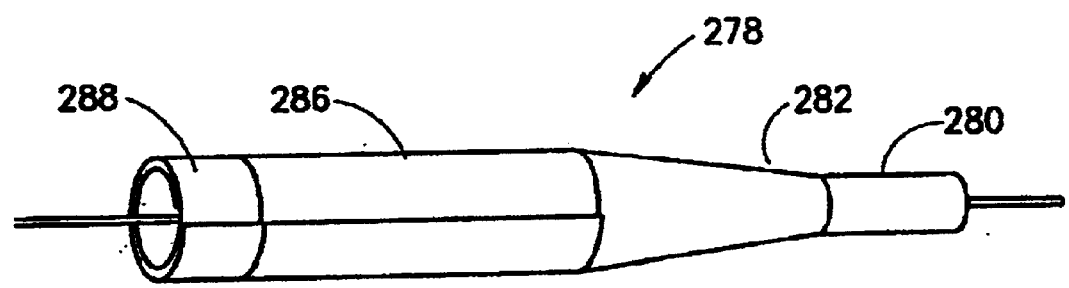
FIGS. 18A and 18B illustrate a device in accordance with the present invention mounted over a guide wire in a collapsed and an expanded position, respectively.
Figure 18B:
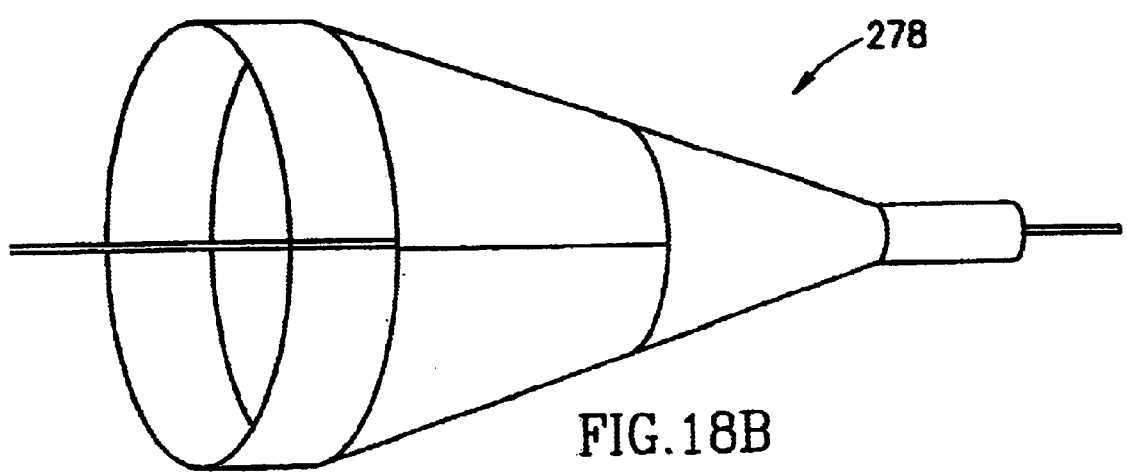

In accordance with a specific embodiment, it is possible to collapse only the rear portion (upstream) of the filter unit, and the anchoring member, without having to collapse a front end of the filtering unit and the trap element. This embodiment is illustrated in FIG. 18 wherein, in FIG. 18A, the filtering device 278 is in its collapsed state with the trap element 280 and a front portion 282 of the filtering unit, being in their normal state, whilst a rear portion 286 of the filtering unit, and the anchoring member 288 are in a collapsed state followed in an overlapping manner as explained with reference to FIG. 17. In FIG. 18B, the device 278 of FIG. 18A is illustrated in its expanded, operative state.

Figure 19A:
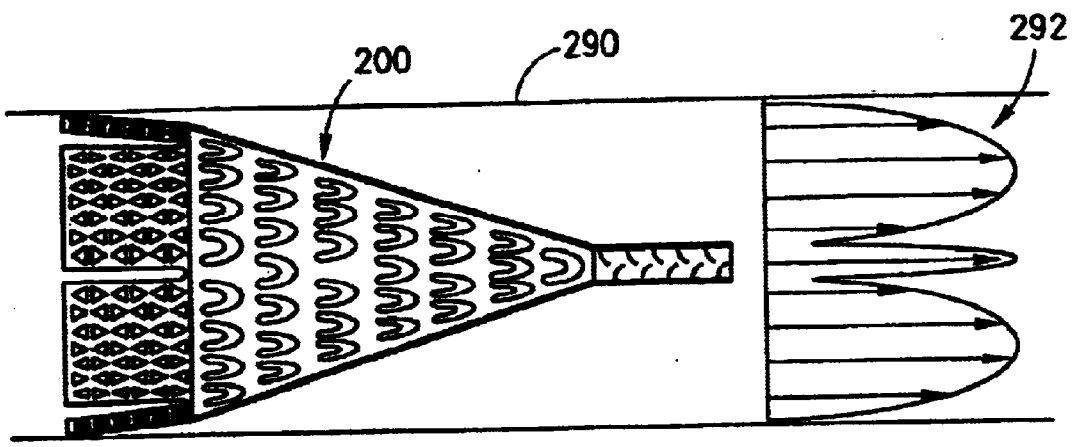
FIG. 19A illustrates a normal, uninterrupted flow position.
Figure 19B:
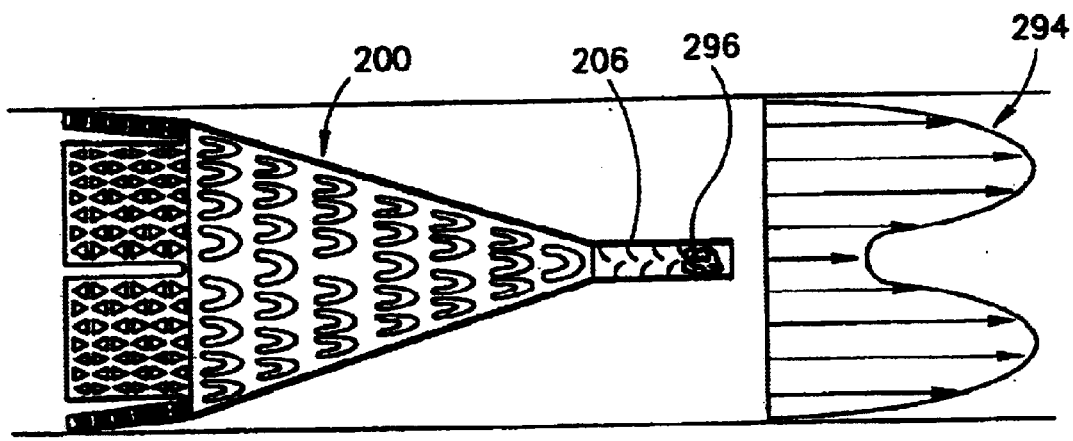
FIG. 19B illustrates a partially occluded position.

Reference is now made to FIG. 19 which illustrate the flow velocity profile of the blood at a section of an artery 290 downstream and adjacent of a filtering device 200 in accordance with the embodiment seen in FIG. 8. The flow velocity profile designated 292 is essentially symmetrical and is obtained in this shape owing to the symmetrical shape of the filtering device 200. The blood flow velocity profile 292 may be obtained by using non-invasive equipment, e.g. ultrasound, micro CT. In FIG. 19B the blood flow velocity profile 294 has a different shape than that seen in FIG. 19A owing to plaque debris 296 occluding the front end of trap element 206 of filtering device 200. The diversity of the flow velocity profile gives indication as to the degree of occlusion of the trap element 206 enabling professional staff to determine when it is necessary to remove the plaque debris entrapped within the trap element.

Figure 20A:
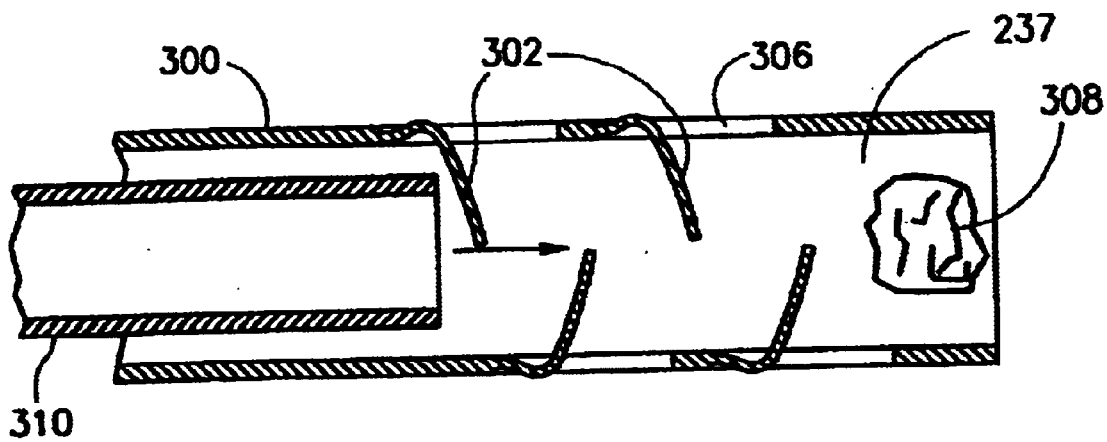
FIGS. 20A–20C illustrate consecutive steps of a method for removal of plaque debris entrapped within the trap element.
Figure 20B:
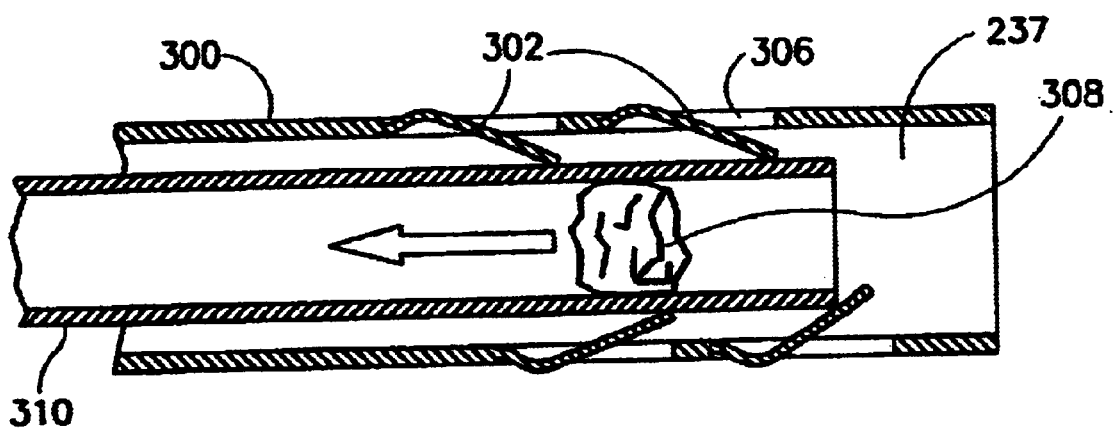
Figure 20C:
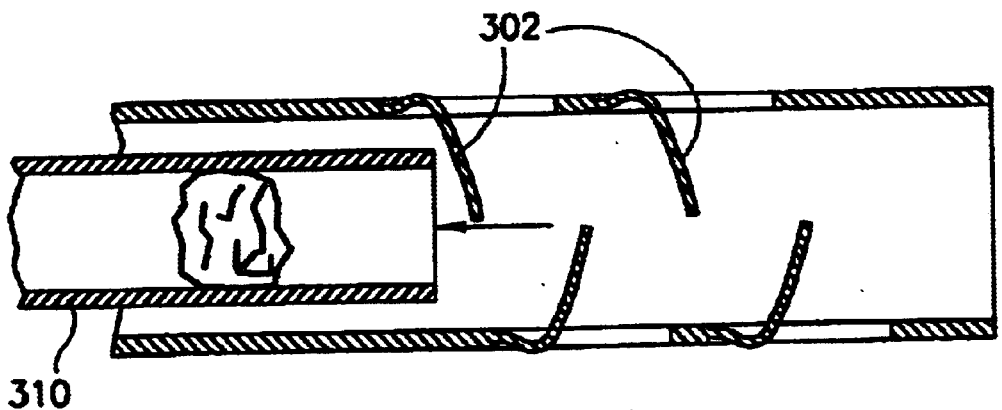

Further reference is being made to FIG. 20, illustrating in somewhat larger scale a front portion of a trap element 300 and a method of removing plaque debris entrapped therebetween. The trap element 300 is cylindrical and comprises a plurality of trapping members 302 extending from the walls of the trap element. Each trapping member 302 has an associated opening 306 in the wall of the trap element for receiving, at least partially, the respective trapping member 302 upon deflection as will be explained with reference to FIG. 20B. Still shown in FIG. 20A, there is a plaque debris 308 situated at a receiving end 237 of the trap element 300.

As explained herein before, upon detection of occlusion or of the presence of plaque debris within the trap element 300, a vacuum catheter 310 is introduced through the wide opening of the filtering device (refer to FIG. 8) and upon introduction thereof into the trap element 300. As seen in FIG. 20B, the trapping members 302 are deformed and are partially received within the openings 306. Vacuum applied within the catheter 310 sucks the plaque debris for removal. Then, upon retraction of the vacuum catheter 310 (see FIG. 20C) the trapping members 302 resume their initial state in which they radially project inwardly.

It will be appreciated that in accordance with any of the above embodiments, upon detecting that a filtering unit has entrapped a certain amount of plaque, and there is danger of blockage of the filtering unit, a suitable suction tube may be inserted percutaneously for evacuation of the entrapped plaque debris.

Some preferred embodiments have been shown and described in the specification. However, it is to be understood that it is not intended thereby to limit the disclosure of the invention, but rather it is intended to cover all modifications and arrangements falling within--the scope and the spirit of the present invention, mutatis mutandis.

For example, a variety of expansion and retraction means may be used for deploying the filtering device. Furthermore, a variety of filtering units may be used which may be manufactured in a variety of different ways and made of different materials.

What is claimed is:

1. An arterial implantable filtering device (200), the device being made of bio-compatible material and comprising a filtering unit (100, 204) for entrapping plaque debris, and an anchoring member (202) engageable with the walls of an artery for anchoring said filtering unit at a fixed location within the artery;

the filtering device (200) is characterized in that the filtering unit (100, 204) has a tapering shape extending between a wide inlet portion and a narrower outlet portion extending downstream, said outlet portion comprising a trap element (206) for entrapping plaque debris, wherein the trap element (206) comprises a tubular body, fixed to the filtering unit (100, 204), and a plurality of elastically deflectable trapping members (230).

2. An implantable filtering device according to claim 1, wherein the filtering unit (204) is formed with a plurality of openings (214) which are sized, shaped and disposed so as to ensure the following parameters:

i) $2 < \text{wall shear stress} < 10^2 [\text{dynes/cm}^2]$ ii) shear rate $< 5000 \, [\text{sec}^{-1}]$.

3. An implantable filtering device according to claim 2, wherein the plurality of openings (214) of the device and their number is such that pressure drop over the filtering device (200) does not exceed about 20 mm Hg.

4. An implantable filtering device according to claim 3, wherein at least a portion of the plurality of openings (214) of the filtering unit (204) is triangularly shaped.

5. An implantable filtering device according to claim 1, wherein the trapping members (230) radially or helically extend from walls (232) of the body (205).

6. An implantable filtering device according to claim 1, wherein the trapping members (230) within the trap element (206) constitutes a maze.

7. An implantable filtering device according to claim 6, wherein the trap (206) element comprises at a downstream end thereof a plurality of deflectable end wires (326) laterally extending across said end.

8. An implantable filtering device according to claim 7, wherein the end wires (326) constitute a grid suitable for entrapping particles larger than about 100 μm.

9. An implantable filtering device according to claim 7, wherein the trapping members (230) and the end wires (236) are deflectable to removably accommodate a guide wire (242) therethrough.

10. An implantable filtering device according to claim 1, wherein the filtering unit (204) is made of a sheet of material formed with a plurality of openings (214).

11. An implantable filtering device according to claim 10, wherein the filtering unit (204) has a conical cross-section.

12. An implantable filtering device according to claim 11, wherein the filtering unit (204) has a conical cross-section being characterized by a tapering rate, said tapering rate is from 1:4 to 1:8.

13. An implantable filtering device according to claim 10, wherein at least part of the openings (214) are formed with a flow directing element (220), outwardly or inwardly projecting from the surface of the filtering unit (204).

14. An implantable filtering device according to claim 13, wherein the flow directing element (220) governs the blood flow profile over the filtering device and at its flow wake.

15. An implantable filtering device according to claim 1, wherein the anchoring member is a stent (56).

16. An implantable filtering device according to claim 15, wherein the filtering unit (52) is integrally connected to the stent (56) by connecting leg members (54).

17. An implantable filtering device according to claim 15, wherein the filtering unit (100) is removably connected to the stent (102).

18. An implantable filtering device according to claim 15, wherein the filtering unit is retained within the stent.

19. An implantable filtering device according to claim 15, wherein the filtering unit is essentially in the shape of a thimble and has at its edge two or more hook members for attachment within the stent.

20. An implantable filtering device according to claim 15, wherein the filtering unit (100) is essentially in the shape of a thimble and has a tapering open end portion adapted for anchoring within a narrowing portion (106) of the stent (102).

21. An implantable filtering device according to claim 1, wherein said anchoring member (202) extends upstream with respect to said filtering unit (204).

22. An implantable filtering device according to claim 1, wherein the filtering unit is suitable for entrapping particles larger than about 100 μm.

23. An implantable filtering device according to claim 1, wherein the filtering unit (100) is a wire braid essentially in the shape of a thimble.

24. An implantable filtering device according to claim 1, wherein at least a portion (286) of the filtering unit, and the anchoring member (288) are inserted into the artery at a collapsed state and are than deployed into an expanded, operative position.

25. An implantable filtering device according to claim 24, wherein at the collapsed state the portion (286) of the filtering unit (278) and the anchoring member (260) are received within a removable insertion tube.

26. An implantable filtering device according to claim 24, wherein at the collapsed state the portion (286) of the filtering unit (278) and the anchoring member (288) are wrapped in an overlapping manner about an longitudinal axis of the device.

27. An implantable filtering device according to claim 24, wherein at the collapsed position the portion (286) of the filtering unit (278) and the anchoring member (260) are axially sectioned, with at least one of the sections being wrapped in an overlapping manner about an longitudinal axis of the device.

28. An implantable filtering device according to claim 24, wherein one or both of the anchoring member (260; 288) and at least the portion (264; 286) of the filtering unit are self-expandable.

29. An implantable filtering device according to claim 28, wherein the filtering unit (100) is removable from the stent (102) by collapsing the tapering portion so as to disengage from the stent.

30. An implantable filtering device according to claim 1, introduced into the artery by either a percutaneous technique or at endarterectomy.

31. An implantable filtering device according to claim 24, wherein one or both of the anchoring member (260; 288) and at least the portion (264; 286) of the filtering unit are balloon expandable.

32. An implantable filtering device according to claim 1, wherein the trap element (300) is formed with a plurality of openings (306), corresponding with the trapping members (302), for accommodating the trapping members (302) at their deflected position.

33. An implantable filtering device according to claim 1, wherein said artery is the carotid artery.

34. A method for detecting occlusion of a filtering device implanted within an artery of an individual, and removal of plaque debris, the method comprising the following steps:
  i) obtaining flow parameter data at the vicinity of a filtering device (200) according to claim 1 in a non-invasive manner;
  ii) processing the flow parameter data to define the extent of occlusion of the trap element (300); and
  iii) introducing a vacuum catheter (310) through the arteries of the individual into the trap element (300), to remove the plaque debris (308).

35. A method according to claim 34, wherein the flow parameter data is either or both of a blood motion spectral signature and a blood velocity profile, both measured downstream of the trap element.

36. An arterial implantable filtering device (200), the device being made of bio-compatible material and comprising a filtering unit (100, 204) for entrapping plaque debris, and an anchoring member (202) engageable with the walls of an artery for anchoring said filtering unit at a fixed location within the artery;
  the filtering device (200) is characterized in that the filtering unit (100, 204) has a tapering shape extending between a wide inlet portion and a narrower outlet portion extending downstream, said outlet portion comprising a trap element (206) for entrapping plaque debris wherein openings (214) of the filtering unit (204) are horseshoe-like shaped oriented such that the legs (216) thereof are upstream.

37. An implantable filtering device according to claim 36, wherein said artery is the carotid artery.

38. A device (120) for removing a filtering unit (100) according to claim 25, comprising at least two flexible hooking members (122) each formed with a sliding portion (124) normally biased into radial expansion and terminating at a hook (126) suitable for engaging the tapering portion of the filtering unit (100), the hooking members (126) being displaceable between a retracted position and an expanded position; a manipulating collar (134) slidingly engaged with the sliding portions (124); whereby axial displacement of the manipulating member (134) entails displacement of the hooking members (126).

39. An implantable filtering device according to claim 1, wherein the trapping members (230; 302) are biased to resume their radial position after deflection thereof.

\* \* \* \* \*